US 8,426,389 B2
Apr. 23, 2013

(12) United States Patent
Reichenbächer et al.

(54) CRYSTALLINE FORM OF R)-3-(4-(2-(2-METHYLTETRAZOL-5-YL)PYRIDIN-5-YL)-3-FLUOROPHENYL)-5-HYDROXYMETHYL OXAZOLIDIN-2-ONE DIHYDROGEN PHOSPHATE

(75) Inventors: Katharina Reichenbächer, Riehen (CH); Robert J. Duguid, Glenmont, NY (US); Jacqueline A. Ware, Troy, NY (US); Douglas Phillipson, Del Mar, CA (US)

(73) Assignee: Trius Therapeutics, Inc., San Diego, CA (US)

( * ) Notice: Subject to any disclaimer, the term of this patent is extended or adjusted under 35 U.S.C. 154(b) by 331 days.

(21) Appl. No.: 12/699,864

(22) Filed: Feb. 3, 2010

(65) Prior Publication Data

US 2010/0227839 A1 Sep. 9, 2010

Related U.S. Application Data

(60) Provisional application No. 61/149,402, filed on Feb. 3, 2009.

(51) Int. Cl.
*A61K 31/675* (2006.01)
*C07D 413/14* (2006.01)

(52) U.S. Cl.
USPC .............................................. 514/89; 546/22

(58) Field of Classification Search ..................... 546/22; 514/89
See application file for complete search history.

(56) References Cited

U.S. PATENT DOCUMENTS

| | | | |
|---|---|---|---|
| 4,128,654 A | 12/1978 | Fugitt et al. | |
| 4,250,318 A | 2/1981 | Dostert et al. | |
| 4,340,606 A | 7/1982 | Fugitt et al. | |
| 4,461,773 A | 7/1984 | Gregory | |
| 4,476,136 A | 10/1984 | Dostert et al. | |
| 4,948,801 A | 8/1990 | Carlson et al. | |
| 5,523,403 A | 6/1996 | Barbachyn | |
| 5,565,571 A | 10/1996 | Barbachyn | |
| 5,652,238 A | 7/1997 | Brickner et al. | |
| 5,688,792 A | 11/1997 | Barbachyn et al. | |
| 6,365,751 B1 | 4/2002 | Gravestock | |
| 6,627,646 B2* | 9/2003 | Bakale et al. ................. | 514/322 |
| 6,689,779 B2 | 2/2004 | Lee et al. | |
| 7,129,259 B2 | 10/2006 | Chen et al. | |
| 7,141,583 B2 | 11/2006 | Gravestock et al. | |
| 7,144,911 B2 | 12/2006 | Flynn et al. | |
| 7,202,257 B2 | 4/2007 | Flynn et al. | |
| 7,396,847 B2 | 7/2008 | Gravestock et al. | |
| 7,462,633 B2 | 12/2008 | Fukuda | |
| 7,473,699 B2 | 1/2009 | Gravestock et al. | |
| 7,498,350 B2 | 3/2009 | Gravestock et al. | |
| 7,816,379 B2 | 10/2010 | Rhee et al. | |
| 2002/0115669 A1 | 8/2002 | Wiedeman et al. | |
| 2003/0166620 A1 | 9/2003 | Lee et al. | |
| 2004/0180906 A1 | 9/2004 | Flynn et al. | |
| 2005/0038092 A1 | 2/2005 | Fukuda | |
| 2005/0107435 A1 | 5/2005 | Gravestock et al. | |
| 2005/0288286 A1 | 12/2005 | Flynn et al. | |
| 2006/0116386 A1 | 6/2006 | Gravestock | |
| 2006/0116400 A1 | 6/2006 | Carcanague et al. | |
| 2006/0270637 A1 | 11/2006 | Gravestock et al. | |
| 2007/0155798 A1 | 7/2007 | Rhee et al. | |
| 2007/0185132 A1 | 8/2007 | Fukuda | |
| 2007/0191336 A1 | 8/2007 | Flynn et al. | |
| 2007/0203187 A1 | 8/2007 | Fukuda | |
| 2007/0208062 A1 | 9/2007 | Carcanague et al. | |
| 2008/0021012 A1 | 1/2008 | Gravestock et al. | |
| 2008/0021071 A1 | 1/2008 | Gravestock et al. | |
| 2008/0064689 A1 | 3/2008 | Carcanague et al. | |
| 2009/0018123 A1 | 1/2009 | Sindkhedkar et al. | |
| 2009/0192197 A1 | 7/2009 | Rhee et al. | |
| 2010/0093669 A1 | 4/2010 | Simson et al. | |
| 2010/0227839 A1 | 9/2010 | Reichenbacher et al. | |

FOREIGN PATENT DOCUMENTS

| | | |
|---|---|---|
| AU | 2004299413 | 7/2009 |
| AU | 2009200606 | 4/2011 |
| CA | 2 549 062 | 7/2011 |
| CN | 101982468 A | 3/2011 |
| EP | 0312000 | 4/1989 |
| EP | 0 352 781 | 1/1990 |
| EP | 1 699 784 | 9/2006 |
| EP | 2 305 657 | 4/2011 |
| EP | 2435051 | 4/2012 |
| IN | 236862 | 11/2009 |
| JP | A-S57-99576 | 6/1982 |

(Continued)

OTHER PUBLICATIONS

Chemical & Engineering News, Feb. 2003, 32-35.*
Brittain ed., "Polymorphism in Pharmaceutical Science.," NY:Marcel Dekker, Inc., 1999, 1-2, 183-226, 235-238.*
U.S. Pharmacopia #23, National Formulary #18, 1995, 1843-1844.*
Muzaffar et al., "Polymorphism and Drug Availability, etc.," J of Pharm. (Lahore), 1979, 1(1), 59-66.*
Jain et al., "Polymorphism in Pharmacy", Indian Drugs, 1986, 23(6) 315-329.*
Taday et al., "Using Terahertz, etc.," J of Pharm. Sci., 92(4), 2003, 831-838.*
Concise Encyclopedia Chemistry, NY: Walter de Gruyter, 1993, 872-873.*
Rowland & Tozer, "Clinical Pharmacokinetics, etc.," 1995, p. 123.*

(Continued)

*Primary Examiner* — Patricia L Morris

(74) *Attorney, Agent, or Firm* — Knobbe, Martens, Olson & Bear LLP

(57) ABSTRACT

A crystalline form of crystalline (R)-3-(4-(2-(2-methyltetrazol-5-yl)-pyridin-5-yl)-3-fluorophenyl)-5-hydroxymethyl oxazolidin-2-one dihydrogen phosphate, methods of making the crystalline form and pharmaceutical compositions comprising the crystalline form are useful antibiotics. Further, the derivatives of the present invention may exert potent antibacterial activity versus various human and animal pathogens, including Gram-positive bacteria such as Staphylococi, Enterococci and Streptococi , anaerobic microorganisms such as Bacteroides and Clostridia, and acid-resistant microorganisms such as Mycobacterium tuberculosis and Mycobacterium avium. Accordingly, the compositions comprising the crystalline form may be used in antibiotics.

27 Claims, 14 Drawing Sheets

FOREIGN PATENT DOCUMENTS

| KR | 11-71107 | 6/2011 |
|---|---|---|
| NZ | 547928 | 9/2009 |
| NZ | 575842 | 2/2011 |
| WO | WO 93/09103 | 5/1993 |
| WO | WO 93/23384 | 11/1993 |
| WO | WO 95/07271 | 3/1995 |
| WO | WO 95/14684 | 6/1995 |
| WO | WO 01/94342 | 12/2001 |
| WO | WO 02/081470 | 10/2002 |
| WO | WO 03/022824 | 3/2003 |
| WO | WO 03/035648 | 5/2003 |
| WO | WO 03/047358 | 6/2003 |
| WO | WO 03/072575 | 9/2003 |
| WO | WO 03/072576 | 9/2003 |
| WO | WO 2004/048350 | 6/2004 |
| WO | WO 2004/083205 | 9/2004 |
| WO | WO 2005/005398 | 1/2005 |
| WO | WO 2005/051933 | 6/2005 |
| WO | WO 2005/058886 | 6/2005 |
| WO | WO 2005/116017 | 12/2005 |
| WO | WO 2006/038100 | 4/2006 |
| WO | WO 2007/023507 | 3/2007 |
| WO | WO 2007/138381 | 12/2007 |
| WO | WO 2010/042887 | 4/2010 |
| WO | WO 2010/091131 | 8/2010 |
| WO | WO 2010/138649 | 12/2010 |

OTHER PUBLICATIONS

Silverman, The Organic Chemistry of Drug Design and Drug Action, NY: Academic Press, 1993, 72-76.*
Ulicky. Comprehensive Dictionary of Physical Chemistry, NY: Prentice Hall, 1992, p. 21.*
Doelker, English translation of Ann. Pharm. Fr., 2002, 60: 161-176, pp. 1-39.*
Doelker, English translation of S.T.P, Pratiques (1999), 9(5), 399-409, pp. 1033.*
Otuska et al., "Effect of Polymorphic, etc.," Chem. Pharm. Bull., 47(6) 852-856 (1999).*
CMU Pharmaceutical polymorphism, internet, p. 1-3 (2002) (print out Apr. 3, 2008).*
Singhal et al., "Drug Polymorphism, etc.," Advanced Drug Delivery reviews 56, p. 335-347 (2004).*
Bae et al., "High-Performance liquid chromatographic analysis of DA-7867, a new oxazolidinone, in human plasma and urine and in rat tissue homogenates", Journal of Chromatography B, 794:397-403 (2003).
Chinese, First Office Action, re Application No. 201010508824.1, dated Jul. 6, 2011.
European Patent Office Communication re Correction of deficiencies noted in the written opinion and amended. Re EPO App. No. 09749235.9, dated Jun. 24, 2011.
International Preliminary Report on Patentability re App. No. PCT/US2010/023122 dated Aug. 9, 2011.
New Zealand Office Action re App. No. 575842, dated Jul. 1, 2011.
Australian Examiner's First Report, dated Oct. 12, 2010, re App. No. 2009200606.
Bae, Soo K., et al. 2007 "Pharmacokinetics of DA-7218, a New Oxazolidinone, and Its Active Metabolite, DA-7157, After Intravenous and Oral Administration of DA-7218 and DA-7157 to Rats", Journal of Pharmacy and Pharmacology 59:955-963.
CA Notice of Allowance re App. No. 2,549,062, dated Apr. 7, 2011.
CA Office Action re App. No. 2,549,062 dated Aug. 21, 2008.
CA Office Action re App. No. 2,549,062 dated Jan. 12, 2011.
CA Office Action re App. No. 2,549,062 dated Mar. 30, 2009.
CN Decision of Rejection re App. No. CN 200480037612.2 dated Jun. 26, 2009.
CN Office Action re App. No. CN 200480037612.2 dated Jan. 9, 2009.
EP Extended Search Report re EP App. No. 10 18 3967, dated Mar. 25, 2011.
EPO Examination Report re App. No. EP 04 80 8458 dated Apr. 30, 2010.
EPO Examination Report re App. No. EP 04 80 8458 dated Aug. 10, 2009.
EPO Supplemental Search Report re App. No. EP 04 80 8458 dated Jul. 24, 2008.
Hiroshi, Nagase ed. Medicinal Chemistry, Technomics, Sep. 25, 1999, The Second Volume, pp. 368-382.
International Partial Search Report re App. No. PCT/US2009/060267, dated Jan. 14, 2010.
International Preliminary Report on Patentability and Written Report, re PCT/US2009/060267 mailed on Apr. 21, 2011.
International Preliminary Report on Patentability for PCT/KR2004/003327 dated Jan. 9, 2006.
International Search Report and Written Opinion re App. No. PCT/US2009/060267, dated May 7, 2010.
International Search Report and Written Opinion re App. No. PCT/US2010/023122 dated Jul. 16, 2010.
International Search Report and Written Opinion re App. No. PCT/US2010/036283 dated Aug. 6, 2010.
International Search Report for PCT/KR2004/003327 dated Mar. 24, 2005. The VPC matter is now closed, no longer in docketing so this will be listed w/002VEP.
International Search Report issued in International Application No. PCT/GB 03/05091 on Aug. 18, 2004.
J. Med. Chem. 32, 1673 (1989).
J. Med. Chem. 33, 2569 (1990).
Japanese Office Action re JP App. No. 2006-545238, dated Sep. 21, 2010.
Mexico Office Action re App. No. PA/a/2006/006955, dated Dec. 10, 2010.
Miyaura, et al.: "Palladium-Catalyzed Cross-Coupling Reactions of Organoboron Compounds", Chemical Reviews, ACS, Washington, DC, US, vol. 95, No. 7, Jan. 1, 1995, pp. 2457-2483.
NZ Examination Report re App. No. 575842 dated Sep. 23, 2010.
NZ Examination Report re App. No. 575842 dated Mar. 31, 2009.
NZ Examination Report re NZ Application No. 589161, dated Nov. 30, 2010.
NZ Office Action re App. No. 575842 dated Jan. 19, 2011.
NZ Office Action re App. No. 575842 dated Jul. 15, 2010.
Prado-Prado, Francisco, J., et al. 2007 "Unified QSAR Approach to Antimicrobials. Part 2: Predicting Activity Against More Than 90 Different Species in Order to Halt Antibacterial Resistance", Bioorganic & Medicinal Chemistry, 15:897-902.
Response to Office Action in Japanese Application No. 2006-545238 dated Apr. 4, 2011.
Rondestvedt, Christian, S., Jr., et al. 1955. "Unsaturated sulfonic acids. V", Journal of the American Chemical Society, 77:6532-6540.
Supplementary European Search Report dated Jul. 31, 2008.
Tetrahedron, vol. 45 No. 5 pp. 1323-1326, 1989 "Chiral Synthesis of Dup 721, A New Antibacterial Agent1, Chia-Lin J. Wang, Walter A. Gregory, and Mark A. Wuonola E.I. Du Pont De Nemours and Company, Inc., Medical Products Department Pharh4aceutical Research and Development Division Experimental Station".
Vera-Cabrera, Lucio, et al. 2006 "In Vitro Activities of DA-7157 and DA-7218 Against *Mycobacterium tuberculosis* and *Nocardia brasiliensis*", Antimicrobial Agents and Chemotherapy 50:3170-3172.
Vera-Cabrera, Lucio, et al. 2006 "In Vitro Activities of the Novel Oxazolidinones DA-7867 and DA-7157 Against Rapidly and Slowly Growing Mycobacteria", Antimicrobial Agents and Chemotherapy 50:4027-4029.
Bae et al., "High-Performance liquid chromatographic analysis of DA-7867, a new oxazolidinone, in human plasma and urine and in rat tissue homogenates", In Journal of Chromatography B, Sep. 5, 2003, 794, p. 397-403.
Office Action in Vietnam Application No. 1-2011-02242, dated Mar. 7, 2012.
Office Action issued in Columbia Application No. 11-097215, dated Oct. 13, 2011.
Office Action issued in Dominican Republic Application No. P2011-0251, dated Jan. 18, 2012.
Dorwald, Side Reactions in Organic Synthesis, 2005, Wiley: VCH Weinheim Preface, pp. 1-15 & Chapter 8, pp. 279-308.
Notice of Opposition issued in Ecuador Application No. SP-11-11285 dated Mar. 9, 2012.

Espinoza-Gonzalez et al., "Efficacy of DA-7218, a new oxazolidinone prodrug, in the treatment of experimental actinomycetoma produced by *Nocardia brasiliensis*", Molecules (Basel, Switzerland) 2008 LNKD-PUBMED: 18259127, vol. 13, No. 1, 2008, pp. 31-40.

Ettmayer, et al.: "Lessons Learned from Marketing and Investigational Prodrugs", J. Med. Chem., (2004), 47(10): 2393-2404.

European Examination Report issued in EP Application No. 10 183 967.8, dated Oct. 24, 2011.

Office Action in European Application No. 10703403.5 dated Jun. 11, 2012.

Office Action issued in U.S. Appl. No. 12/577,089, dated Jun. 4, 2012.

Stella, "Prodrugs as therapeutics", Expert Opin. Ther. Patents (2004), 14(3): 277-280.

Testa, "Prodrug research: futile or fertile?", Biochemical Pharmacology, 68 (2004): 2393-2404.

Office Action issued in U.S. Appl. No. 12/577,089, dated Mar. 19, 2012.

Office Action issued in U.S. Appl. No. 12/211,655, dated Feb. 10, 2012.

Office Action issued in U.S. Appl. No. 12/211,655, dated Nov. 3, 2011.

Restriction Requirement issued in U.S. Appl. No. 12/787,293 dated May 24, 2012.

Wolff, et al.: "Metabolic Considerations in Prodrug Design", Burger's Medicinal Chemistry and Drug Discovery, 5th ed. vol. 1: Principles and Practice, pp. 949-982.

* cited by examiner

| FIG. 4-1 |
| FIG. 4-2 |
| FIG. 4-3 |

MANUFACTURING PROCESS SCHEMATIC FOR TR-701 FA FOR INJECTION
200 MG/VIAL: STERILE FILTERING, FILLING, AND LYOPHILIZATION

CRYSTALLINE FORM OF R)-3-(4-(2-(2-METHYLTETRAZOL-5-YL)PYRIDIN-5-YL)-3-FLUOROPHENYL)-5-HYDROXYMETHYL OXAZOLIDIN-2-ONE DIHYDROGEN PHOSPHATE

This application claims priority to U.S. Provisional Application No. 61/149,402, filed Feb. 3, 2009, which is incorporated herein by reference in its entirety.

BACKGROUND OF THE INVENTION

1. Field of the Invention

The present disclosure relates to a crystalline form of (R)-3-(4-(2-(2-methyltetrazol-5-yl)pyridin-5-yl)-3-fluorophenyl)-5-hydroxymethyl oxazolidin-2-one dihydrogen phosphate, and methods of making and using the crystalline form. The crystalline form may be used as a pharmaceutically active compound in compositions that are useful in impeding the growth of bacteria or treating patients suffering from bacterial infections.

2. Description of the Related Art

US Patent Publication No. 20070155798, which is hereby incorporated by reference in its entirety, recently disclosed a series of potently anti-bacterial oxazolidinones including

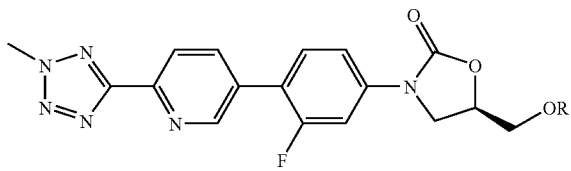

wherein R=H, PO(OH)$_2$, and PO(ONa)$_2$.

Although this patent application discloses methods of making compounds such as the free acid (wherein R=PO(OH)$_2$) and the disodium salt (wherein R=PO(ONa)$_2$), there is no indication that any of the compounds were stably crystallized or purified. In addition, these processes include the use of reagents which are highly corrosive, such as trichloroacetic acid, or explosive, such as ethyl ether, and therefore are not suitable for commercial use. As discussed below in more detail, attempts to crystallize the disodium salt by the instant inventors resulted in a highly hygroscopic, unstable crystalline salt form which turned amorphous upon drying.

There is a need in the art for a stable, non-hygroscopic crystalline form of the free acid (wherein R=PO(OH)$_2$) or a salt thereof that can be accurately poured and weighed for use in pharmaceutical formulations. Also, it would be advantageous if the crystalline form did not form a large number of polymorphs, as the number of polymorphs hinders the ability to reproducibly provide the identical polymorph during manufacturing. Making a particular crystalline form having these properties is an empirical process, and one skilled in the art would be unable to predict among the free acid form of the pharmaceutical compound or one of the corresponding salts, which would crystallize, if at all, under which crystallization conditions. In addition, one skilled in the art would be unable to predict which crystalline form would have the beneficial properties of stability, pourability, non-hygroscopicity and reproducibility.

In addition, improved methods of making the free acid are disclosed in U.S. patent application Ser. No. 12/577,089, which is assigned to Trius Therapeutics, Inc., and which is incorporated herein by reference. Difficulties in filtering crystalline material and processing the crystalline material into dosage forms, such as tablets, have arisen because the free acid forms fine particles which delay processing time. Therefore, there is also a need in the art for a crystalline form of the compound and related methods that overcome these processing difficulties.

In addition, it would be advantageous to have a purified compound that is suitable for pharmaceutical compositions.

SUMMARY OF THE INVENTION

Surprisingly, a crystalline (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$), was more stable and non-hygroscopic than the salt forms that were tested. In addition, unlike typical crystallizations, where the crystallization conditions, such as the solvent and temperature conditions, determine the particular crystalline form, the same crystalline form of 1 (R=PO(OH)$_2$) was produced using many solvent and crystallization conditions. Therefore, this crystalline form was very stable, was made reproducibly, and ideal for commercial production because it reduced the chances that other polymorphs would form contaminating impurities during production. However, in all preliminary testing, the free acid crystallized as fine particles, making filtering and processing difficult.

To overcome difficulties in filtering and processing crystalline (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$), processes described herein result in significantly reduced filtering time, avoid more toxic solvents, and significantly increased ease of preparing dosage forms such as tablets. It has been found that implementing various processes can control the particle size distribution of the resulting material, which is useful for making the crystalline form, and for commercial production and pharmaceutical use. Surprisingly, the process for increasing the particle size reduces the amount of the dimer impurity, in comparison to the process for making the free acid disclosed in U.S. patent application Ser. No. 12/577,089. Thus, various methods of making and using the crystalline form are also provided.

In addition, by using methods of making the free acid disclosed in U.S. patent application Ser. No. 12/577,089, which is assigned to the same assignee as in the present application, and by using the crystallization methods described herein, a crystalline free acid having at least 96% purity by weight may be formed that comprises a compound having the following formula:

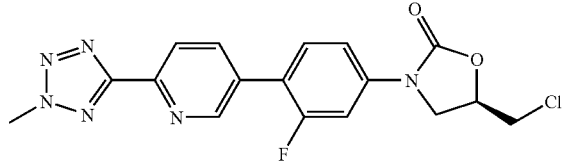 [SMILES: Cn1nnc(-c2ccc(-c3ccc(N4C[C@H](CCl)OC4=O)cc3F)cn2)n1]

(hereinafter "the chloro impurity"), i.e., (R)-5-(chloromethyl)-3-(3-fluoro-4-(6-(2-methyl-2H-tetrazol-5-yl)pyridin-3-yl)phenyl)oxazolidin-2-one in an amount less than 1%.

Similarly, by using methods of making the free acid disclosed in U.S. patent application Ser. No. 12/577,089, which is assigned to the same assignee as in the present application, and by using the crystallization methods described herein, a crystalline free acid having at least 96% purity by weight may be formed that comprises a compound having the following formula:

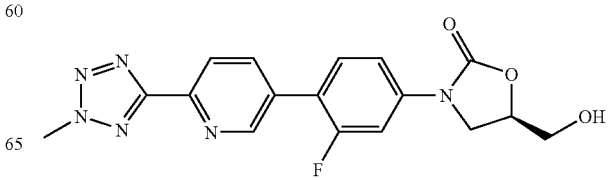

(hereinafter "TR-700"), i.e., 5R)-3-{3-Fluoro-4-[6-(2-methyl-2H-1,2,3,4-tetrazol-5-yl)-pyridin-3-yl]-phenyl}-5-hydroxymethyl-1,3-oxazolidin-2-one, in an amount less than 1%.

The crystalline free acid may have one or more of the attributes described herein.

In some aspects, a purified crystalline (R)-3-(4-(2-(2-methyltetrazol-5-yl)-pyridin-5-yl)-3-fluorophenyl)-5-hydroxymethyl oxazolidin-2-one dihydrogen phosphate, i.e., the free acid, has a purity of at least about 96% by weight. In some embodiments, the crystalline free acid has a median volume diameter of at least about 1.0 μm.

In some embodiments, pharmaceutical composition comprises the free acid or a salt thereof and at least one pharmaceutically acceptable carrier, excipient or diluent.

In some embodiments, a method of treating a bacterial infection comprises administering an effective amount of the crystalline free acid, or a salt thereof to a subject in need thereof. Methods may also include comprise treating a bacterial infection comprising administering the free acid, pharmaceutical composition thereof or a salt to a subject in need thereof.

In some aspects, processes for making the free acid comprise drying crystallized (R)-3-(4-(2-(2-methyltetrazol-5-yl)pyridin-5-yl)-3-fluorophenyl)-5-hydroxy-methyl oxazolidin-2-one dihydrogen phosphate, or a pharmaceutical composition comprising the salt thereof.

These and other embodiments are described in greater detail below.

Figure 1:
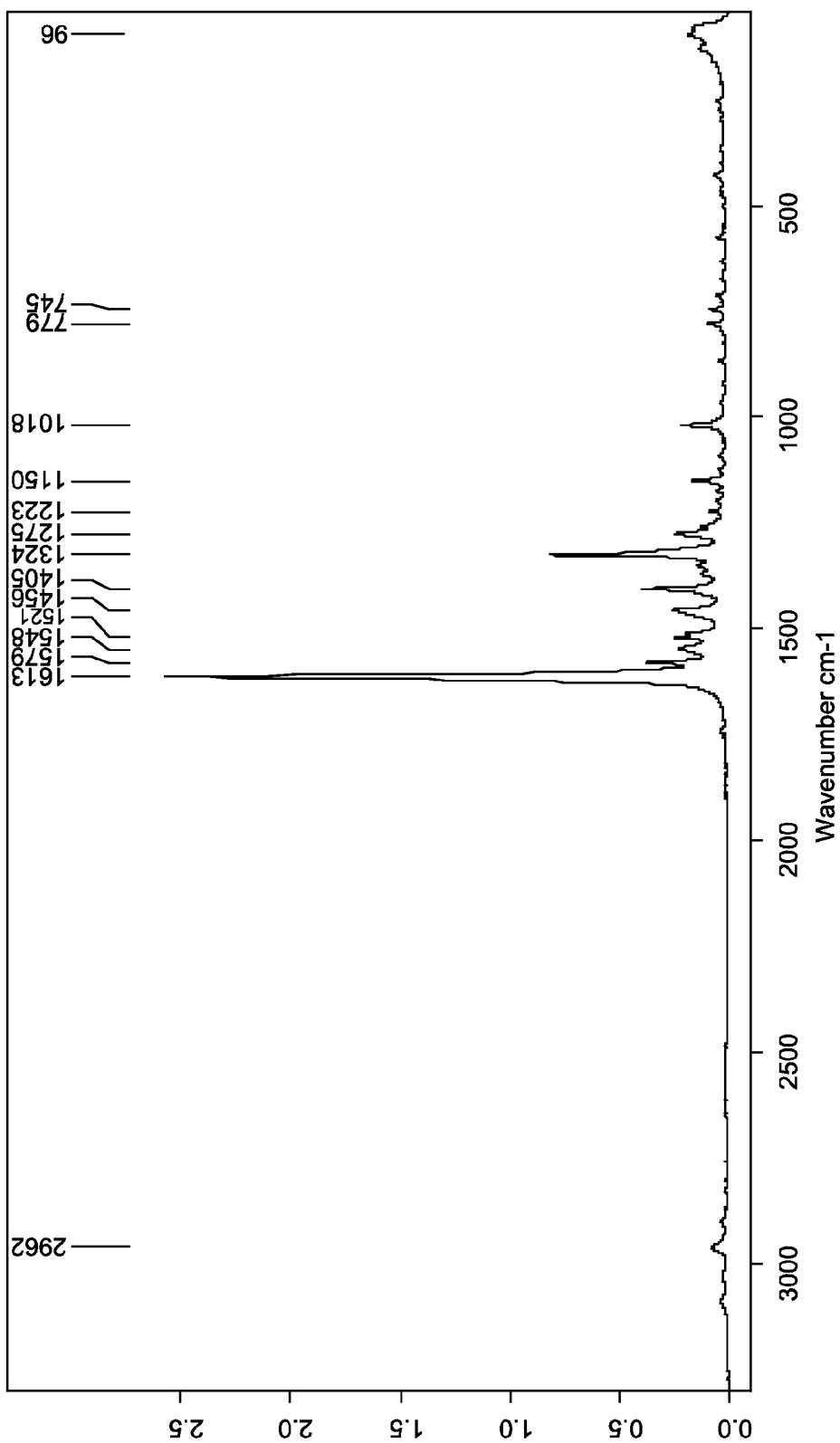
FIG. 1 the FT-Raman spectrum of crystalline 1 (R=PO(OH)$_2$).

DETAILED DESCRIPTION OF THE PREFERRED EMBODIMENT (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$), which is sometimes referred to herein as the "free acid" or "TR-701 FA," and several salts thereof were prepared under various crystallization conditions to determine which of the materials would form the most stable and least hygroscopic crystalline compound. The empirical process of making crystalline forms of the free acid and salts thereof resulted in the selection of a crystalline free acid that, in addition to superior stability and non-hygroscopicity, was reproducibly made under various crystallization conditions, which was subsequently purified and dried.

Specifically, most of the salts that were evaluated were difficult to prepare in a crystalline form or were otherwise unstable, such as in a purified or dried form. For example, with respect to the mono-sodium salt, the formation of a stable hydrate was not detected. Also, the material contained over 10% by weight of water and therefore the material was very hygroscopic, and thus not suitable for the desired use.

A disodium salt crystalline hydrate was formed, but was unstable and contained 19.6% by weight of water. The disodium salt, however, was very soluble. Drying the hydrate resulted in amorphous samples. The water content of an amorphous sample was about 6.2% by weight.

A crystalline solid material was not isolated for a di-potassium.

A hemi-calcium salt was prepared as a crystal, however, it was unsuitably hygroscopic.

A hemi-magnesium salt crystalline material was formed and appeared to contain various hydrates of a salt, and therefore, the presence of various polymorphs would render it less desirable for use in a formulation. In one experiment, a magnesium salt had a melting point of 152.8° C., which in this case indicated that this material was less stable in comparison to the free acid.

The free acid formed crystals, which were non-hygroscopic upon filtering and drying, which showed an aqueous solubility of 0.1 mg/ml (pH=3.2 of the saturated solution). The crystalline material's melting point was approximately 255-258° C., and therefore was very stable at a relatively high temperature.

Generally, the crystallization conditions are usually critical for forming a particular polymorph; however, surprisingly, the same free acid polymorph was formed under all of the various conditions in which the crystalline free acid was formed.

In some embodiments, the crystalline material is non-hygroscopic, so it does not readily take up and retain water from the atmosphere. In some embodiments, "non-hygroscopic" material has a water content of less than about 5%, 4%, 3%, 2%, 1%, 0.9%, 0.8%, 0.7%, 0.6%, 0.5%, 0.4%, 0.3%, 0.2%, or 0.1% water by weight.

Advantageously, the free acid can be used to make both a solid formulation and an intravenous (IV) formulation. During the evaluation, it was found that the disodium salt, although unsuitable for solid compositions such as tablets, was very soluble and therefore suitable for IV formulations. Thus, in another embodiment, a sterile lyophilized powder for injection is made by forming a disodium salt in situ with sodium hydroxide and lyophilizing the resulting solution. The disodium salt is highly soluble and therefore is advantageous to reconstitute in sterile water to yield a solution. In some embodiments, the resulting solution may be added to an intravenous bag. The bag may contain an isotonic solution such as 0.9% sodium chloride or 5% dextrose.

In some embodiments, the salt solution, such as a disodium or monosodium salt, can be lyophilized by freezing the solution in a lyophilizer to about −50 to −30° C. at about 0.1 to 1 degree/minute and holding it for about 200-700 minutes at which point the chamber in the lyophilizer is evacuated to approximately 200-250 millitorr and the temperature is ramped up to about −30 to about −10° C. at about 0.5 to about 3 degrees/minute. The product is held at −30 to about −10° C. for about 1000-2500 minutes and then the temperature is ramped up to about 21-35° C. at about 0.1 to 1 degrees/minute and held for 1000-2500 minutes to give the finished product.

In embodiments of some preparation methods, the crystalline free acid (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$) can be prepared by acidification of an aqueous solution of the corresponding salt, such as the disodium salt 1 (R=PO(ONa)$_2$).

Any salt of the free acid 1 (R=PO(OH)$_2$) can be used to regenerate the free acid by acidification. In some embodiments, the salt is an alkali metal or an alkaline earth metal. In other embodiments, the salt is an alkali metal salt, such as a disodium salt of 1 (R=PO(OH)$_2$).

It was found that the choice of acid is not critical. Any acid that is sufficiently acidic to doubly protonate the phosphate disodium salt 1 (R=PO(ONa)$_2$), or other salt, to yield the free acid 1 (R=PO(OH)$_2$) can be used. In some embodiments, the acid is HCl, HBr, or H$_2$SO$_4$.

After dissolving the salt of the (R)-3-(4-(2-(2-methyl]tetrazol-5-yl)-pyridin-5-yl)-3-fluoro-phenyl)-5-hydroxy-methyl oxazolidin-2-one dihydrogen phosphate, and after, acidifying the salt solution to form crystals, the crystals may be filtered from the supernatant. In some embodiments, wet crystals may be dried, for example by using a vacuum or lyophilizing the crystals.

In some embodiments, crystalline refers to uniformly crystalline material of crystalline (R)-3-(4-(2-(2-methyltetrazol-5-yl)pyridin-5-yl)-3-fluorophenyl)-5-hydroxymethyl oxazolidin-2-one dihydrogen phosphate, such as substantially pure crystals.

The terms "approximately, "about," and "substantially" as used herein represent an amount close to the stated amount that still performs the desired function or achieves the desired result. For example, the terms "approximately," "about" and "substantially" may refer to an amount that is within less than 10% of, within less than 5% of, within less than 1% of, within less than 0.1% of, and within less than 0.01% of the stated amount.

For instance, in the pharmaceutical industry, it standard practice to provide substantially pure material when formulating pharmaceutical compositions. Therefore, in some embodiments, "substantially pure" refers to the amount of purity required for formulating pharmaceuticals, which may include, for example, a small amount of amorphous material or other material, wherein the material may still achieve sufficient pourability, lack of hygroscopicity, and purity suitable for pharmaceutical use. In some embodiments, the crystalline free acid that is substantially pure contains at least about 96% crystalline free acid by weight, such as at least about 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% crystalline free acid by weight. In some embodiments, the di- or mono-sodium salt in formulations described herein have at least about 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 97.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, or 100% crystalline salt by weight. In formulating pharmaceuticals, it is useful to provide a non-sticky solid crystalline (R)-3-(4-(2-(2-methyltetrazol-5-yl)pyridin-5-yl)-3-fluorophenyl)-5-hydroxymethyl oxazolidin-2-one dihydrogen phosphate that can be poured and accurately weighed for use in, for example, tablets and capsules. Therefore, in some embodiments, the crystalline material is in a pourable form such that the particles do not strongly adhere to each other or the vessel in which it is contained, such that it is capable of uniformly and steadily flowing from a vessel.

Preparation of the free acid (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$), and of its disodium salt 1 (R=PO(ONa)$_2$) is described in US Patent Publ. No. 2007/0155798 and U.S. patent application Ser. No. 12/577,089, the latter of which is assigned to the same assignee as in the present application.

In embodiments of some preparation methods, the crystalline free acid (R)-3-(4-(2-(2-methyltetrazol-5-yl)pyridin-5-yl)-3-fluorophenyl)-5-hydroxymethyl oxazolidin-2-one dihydrogen phosphate 1 (R=PO(OH)$_2$) can be prepared by acidification of an aqueous solution of the corresponding salt, such as the disodium salt 1 (R=PO(ONa)$_2$). Any salt of the free acid 1 (R=PO(OH)$_2$) can be used to regenerate the free acid by acidification. In some embodiments, the salt is an alkali metal or an alkaline earth metal. In other embodiments, the salt is an alkali metal salt, such as a disodium salt of 1 (R=PO(OH)$_2$).

In additional embodiments of some preparation methods, the free acid itself can be used to prepare the crystalline form by dissolution in a dissolution solvent, such as a dipolar aprotic solvent, for example dimethyl sulfoxide (DMSO) or 1-methyl-2-pyrrolidone (NMP) followed by addition of a crystallization-inducing solvent such as ethanol, acetone, acetonitrile, dioxane, heptanes, isopropyl alcohol, methanol, tetrahydrofuran, toluene, water, dichloromethane, methyl isobutyl ketone and ethyl acetate. In some embodiments, the dissolution and the crystallization-inducing solvents can be either a pure solvent or a mixture of pure solvents, and can be either in the form of a liquid, a vapor, or a second layer. In some embodiments of the latter two cases, the crystallization-inducing solvent can be employed according to the vapor diffusion method of growing crystals, or the solvent-layering method, both of which are well-known to those of skill in the art.

In further embodiments of some preparation methods, the free acid can be dissolved in at least one dipolar aprotic solvent such as DMSO or NMP at an elevated temperature, and crystalline free acid 1 (R=PO(OH)$_2$) obtained by cooling of the resulting solution, according to methods well-known to those of skill in the art. The solvent can either be pure, or itself a mixture of pure solvents In formulating pharmaceuticals, it is useful to provide a solid crystalline compound that can be easily formed into dosage forms, for example, tablets. In addition, it is useful to shorten the length of time necessary to make a compound. To address these needs, in some embodiments, a method of making crystalline 1 (R=PO(OH)$_2$) that results in increased particle size are disclosed that significantly decrease the filtering time caused by fine particles that slow down the filtering step. In further embodiments, crystalline 1 (R=PO(OH)$_2$) has a particular particle size distribution, for example, that directly results from the method without relying on sieving the material solely to obtain the particle size distribution.

To this end, in some embodiments, the resulting larger particle size of the crystalline 1 (R=PO(OH)$_2$) may be made by a high temperature precipitation procedure. In addition, in embodiments wherein an acid is used to form the free acid from the salt, it was found that the increasing the rate at which the reaction mixture was added to the acid affects the particle size and makes the particles larger. Thus, in some embodiments, the reaction mixture may be contacted to the acid solution as fast as possible, such that there is essentially immediate contact with the acid solution. In conventional methods, the reaction mixture made contact with the acid solution more slowly, because the acid solution was added to the reaction mixture and therefore the reaction mixture may not contact the acid solution until some time after addition of the acid solution, causing much smaller particle size. It was found that reversing the step, that is, adding the reaction mixture to the acid solution, will allow the reaction mixture to effectively immediately contact the acid over the course of introducing the reaction mixture to the acidic solution, which results in larger particle size material. Thus, in some embodiments, immediate contact is made by adding the reaction mixture to the acid solution. The reaction mixture may be pumped into the acid solution over time, for example, over a few hours, such as 1-4 hours.

In some embodiments, an aqueous ethanol- or THF-containing solution of TR-701FA may be prepared by adding a sodium bicarbonate solution, for example, a 2-10% solution by weight, such as a 5% solution. In some embodiments, the solution may be added to an aqueous acidic solution and ethanol or THF to form the free acid. In some embodiments, from about 0.5-10, about 1.5-3.0, or about 2.2 equivalents of 1 M HCl may be used. In addition, in some embodiments, about 1-10 volumes, about 2-6 volumes, or about 4 volumes of ethanol may be used. THF may also be used. In some embodiments, the solution including the hydrochloric acid and ethanol may be maintained at about 40-100° C., about 60-70° C., or about 65 to 70° C. The acid and alcohol may be adjusted. The TR-701FA crystallized during this addition with a reduced amount of fines in the product in comparison to previously disclosed methods.

In some embodiments, the ethanol or THF prevents the free acid from gelling during the process.

Typical particle size distribution is measured using a laser diffraction particle size analyzer, namely a Malvern Mastersizer. D10 (μm) represents the diameter below which lies 10% of the total particle volume. D50 (μm) is the median volume diameter. D90 (μm) is the diameter below which lies 90% of the total particle volume.

In some embodiments, when the particle size is not controlled, 10% of the total particle volume may have a diameter of less than about 0.28 μm, the median volume diameter may be about 0.79 μm, and 90% of the total particle volume may have a diameter of less than about 0.44 μm. By controlling (increasing) the particle size using methods disclosed herein, the particles are significantly larger overall.

In some embodiments, when the particle size is controlled using the methods described herein to increase particle size, 10% of the total particle volume may have an average diameter of at least about 0.5 μm, and/or the median volume diameter may be at least about 1.0 μm, and/or 90% of the total particle volume may have an average diameter of at least about 45 μm. In some embodiments, when the particle size is controlled (to increase particle size), 10% of the total particle volume may have an average diameter of about 0.5-10 μm, such as about 1-5 μm. For example, when the particle size is controlled (to increase particle size), 10% of the total particle volume may have an average diameter of about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 μm.

In some embodiments, when the particle size is controlled (to increase particle size), the median volume diameter may be greater than about 1.0 μm, and have an average median volume diameter about 1-44 μm, about 1-40 μm, about 10-35 μm, about 20-30 μm, or about 25-29, such as about 27 μm. In some embodiments, when the particle size is controlled to increase particle size, the average median volume diameter may be about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 38, 39, 40, 41, 42, 43, or 44 μm. For example, the average median volume diameter may be about 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, 27, 27.1, 27.2, 27.3, 27.4, 27.5, 27.6, 27.7, 27.8, 27.9, 28, 28.1, 28.2, 28.3, 28.4, 28.5, 28.6, 28.7, 28.8, 28.9, or 29 μm.

In some embodiments, when the particle size is controlled (to increase particle size), 90% of the total particle volume may have an average diameter of the least about 45 μm such as about 45-100, about 45-80, about 55-75, or about 64-68 such as about 66. In some embodiments, when the particle size is controlled, 90% of the total particle volume may have an average diameter of about 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 μm. For example, 90% of the total particle volume may have an average diameter of about 64, 64.1, 64.2, 64.3, 64.4, 64.5, 64.6, 64.7, 64.8, 64.9, 65, 65.1, 65.2, 65.3, 65.4, 65.5, 65.6, 65.7, 65.8, 65.9, 66, 66.1, 66.2, 66.3, 66.4, 66.5, 66.6, 66.7, 66.8, 66.9, 67, 67.1, 67.2, 67.3, 67.4, 67.5, 67.6, 67.7, 67.8, 67.9, or 68 μm.

Figure 2:
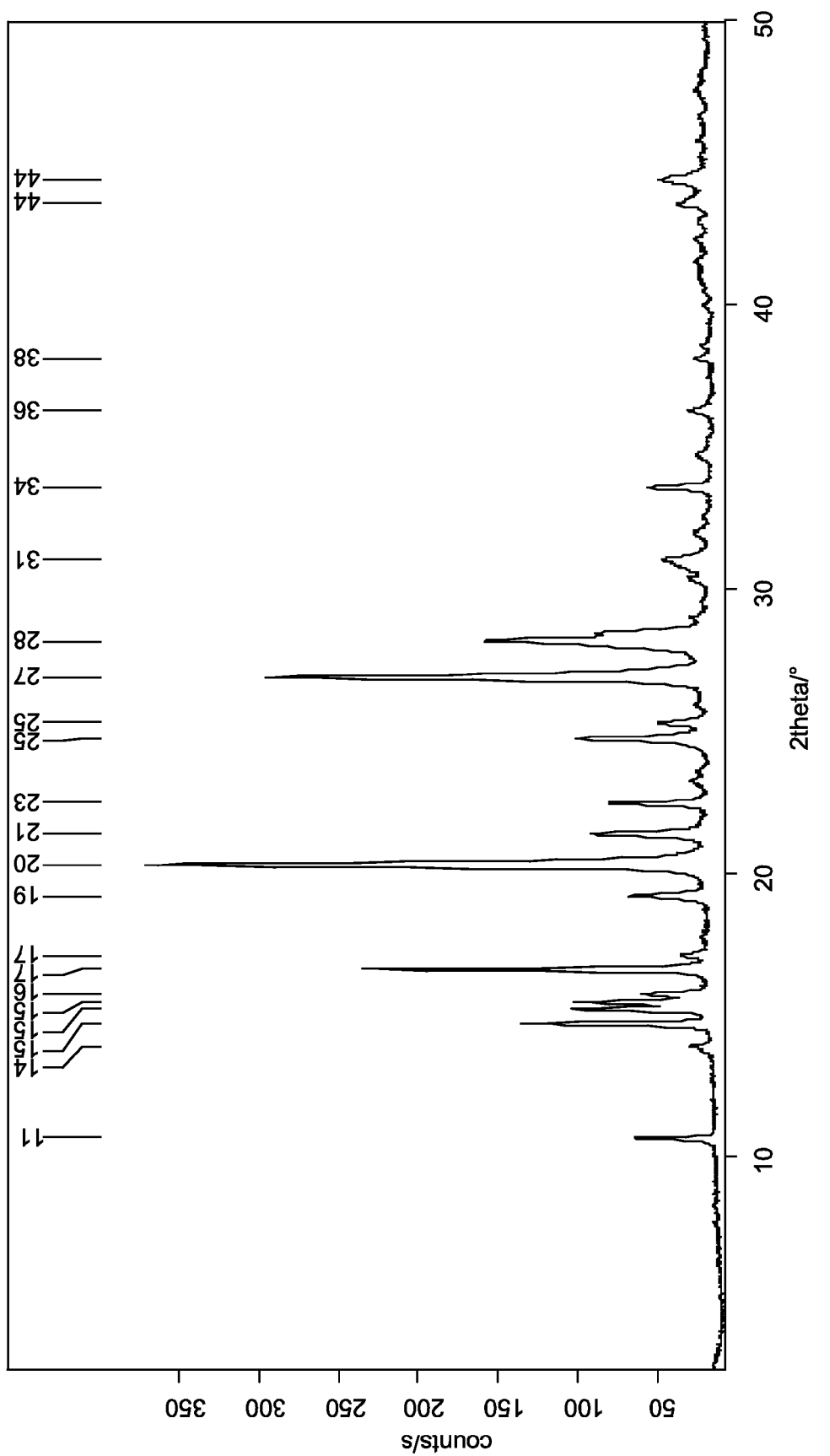
FIG. 2 shows the X-ray powder pattern of crystalline 1 (R=PO(OH)$_2$).

The crystalline free acid 1 (R=PO(OH)$_2$) may be characterized in having the FT-Raman for example as shown in FIG. 1, and the X-ray powder diffraction for example as shown in FIG. 2, with the corresponding numerical data for example as shown in Table 1 and Table 2 respectively. FIG. 3, FIG. 4, FIG. 5 and FIG. 6 show examples of the differential scanning calorimetry (DSC) thermogram, solution $^1$H NMR spectrum, the TG-FTIR diagram, and the dynamic vapor sorption (DVS) behavior of crystalline 1 (R=PO(OH)$_2$) respectively.

TABLE 1

FT-Raman spectroscopic data for crystalline free acid 1 (R = PO(OH)$_2$)

| Wavenumber (cm-1) | Absolute Intensity |
| --- | --- |
| 1612.9 | 2.57 |
| 1579.0 | 0.38 |
| 1521.3 | 0.25 |
| 1455.8 | 0.26 |
| 1404.9 | 0.39 |
| 1324.4 | 0.82 |
| 1274.7 | 0.24 |
| 1149.9 | 0.17 |
| 1018.3 | 0.22 |

TABLE 2

X-ray powder pattern diffraction data for crystalline free acid 1 (R = PO(OH)$_2$)

| Angle 2Theta/° | Intensity/% |
| --- | --- |
| 10.6 | 17 |
| 13.7 | 6 |
| 13.9 | 8 |
| 14.7 | 38 |
| 15.2 | 28 |
| 15.4 | 28 |
| 15.7 | 16 |
| 16.6 | 65 |
| 17.1 | 10 |
| 19.2 | 19 |
| 20.3 | 100 |
| 21.4 | 25 |
| 22.4 | 23 |
| 23.2 | 8 |
| 23.6 | 7 |
| 24.7 | 29 |
| 25.3 | 14 |
| 25.9 | 8 |
| 26.8 | 82 |
| 28.2 | 44 |
| 28.4 | 24 |
| 29.0 | 8 |

TABLE 2-continued

X-ray powder pattern diffraction data for crystalline free
acid 1 (R = PO(OH)$_2$)

| Angle 2Theta/° | Intensity/% |
|---|---|
| 30.3 | 8 |
| 30.8 | 11 |
| 31.0 | 13 |
| 31.9 | 8 |
| 33.5 | 17 |
| 34.7 | 7 |

In some embodiments, the distinguishing peaks for the crystalline free acid comprise the following peaks: 14.7°, 15.2°, 16.6°, 20.3°, 26.8°, and 28.2°.

In other embodiments, the distinguishing peaks for the crystalline free acid comprise the following peaks: 10.6°, 13.9°, 14.7°, 15.2°, 16.6°, 20.3°, 26.8°, and 28.2°.

In some embodiments, the crystalline free acid comprises impurities that are present in less than 1% of the purified crystalline free acid. These impurities include

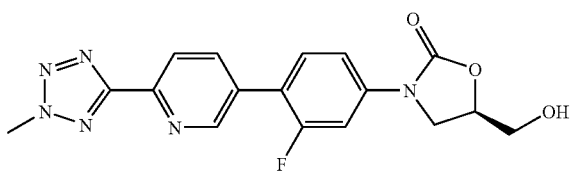 [SMILES: Cn1nnc(-c2ccc(-c3ccc(N4C[C@H](CO)OC4=O)cc3F)cn2)n1]

i.e., 5R)-3-{3-Fluoro-4-[6-(2-methyl-2H-1,2,3,4-tetrazol-5-yl)-pyridin-3-yl]-phenyl}-5-hydroxymethyl-1,3-oxazolidin-2-one ("TR-700") and/or

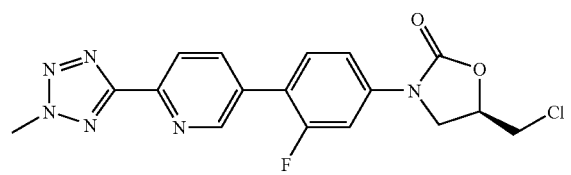 [SMILES: Cn1nnc(-c2ccc(-c3ccc(N4C[C@H](CCl)OC4=O)cc3F)cn2)n1]

i.e., (R)-5-(chloromethyl)-3-(3-fluoro-4-(6-(2-methyl-2H-tetrazol-5-yl)pyridin-3-yl)phenyl)oxazolidin-2-one ("chloro impurity").

Of the conventionally produced material having impurities that were identified using HPLC in Example 15, at least 2% by weight of the chloro impurity was present. In purified crystalline free acid made using the method of making the free acid disclosed in U.S. patent application Ser. No. 12/577,089, which is assigned to the same assignee as in the present application, and the crystallization methods disclosed herein, the chloro impurity was present in less than about 1% by weight, such as less than about 0.9%, 0.8%, 0.7%, 0.6%, 0.5%, 0.4%, 0.3%, 0.2%, or 0.1% by weight of the of the crystalline free acid. In some embodiments the chloro impurity may be reduced to much lower than 0.1% by weight, such as, less than about 0.09%, 0.08%, 0.07%, 0.06%, 0.05%, 0.04%, 0.03%, 0.02%, or 0.01% by weight of the crystalline free acid. In some embodiments, the purified crystalline free acid is substantially free of the chloro impurity.

Of the conventionally produced material having impurities that were identified using HPLC in Example 15, at least about 1% by weight of the TR-700 impurity was present. In purified crystalline free acid made using the method of making the free acid disclosed in U.S. patent application Ser. No. 12/577,089, which is assigned to the same assignee as in the present application, and the crystallization methods disclosed herein, the TR-700 impurity was present in less than about 1% by weight. In some embodiments, the crystalline free acid contains less than about 0.9%, 0.8%, 0.7%, 0.6%, 0.5%, 0.4%, 0.3%, 0.2%, or 0.1% by weight of the TR-700 impurity. In some embodiments, the crystalline free acid is substantially free of the TR-700 impurity.

In addition, purified crystalline free acid made using the method of making the free acid disclosed in U.S. patent application Ser. No. 12/577,089, which is assigned to the same assignee as in the present application, and the crystallization methods disclosed herein, may also be distinguished from the conventionally produced crystalline free acid by the presence of the following compounds. For example, the following impurities were not found in a sample of conventionally produced crystalline free acid as shown in Example 15:

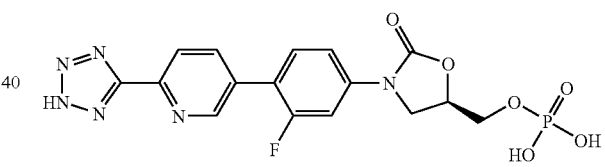

(hereinafter "des-methyl TR-701"), i.e., dihydrogen ((5R)-3-{3-fluoro-4-[6-(2H-1,2,3,4-tetrazol-5-yl)-3-pyridinyl]phenyl}-2-oxo-1,3-oxazolan-5-yl)methyl phosphate;

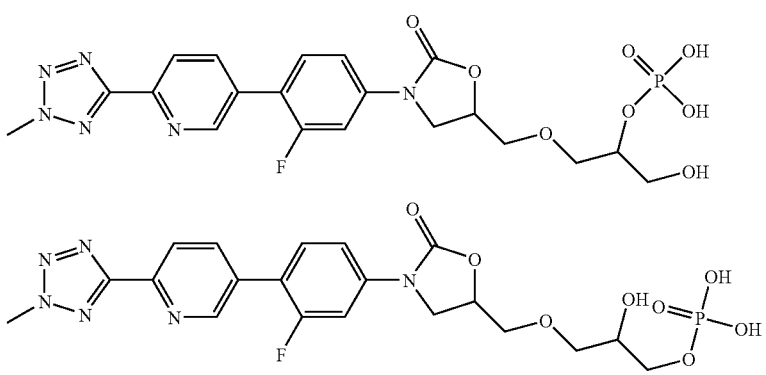

(hereinafter "overalkylated-phosphorylated impurity"), i.e., 51-((3-(3-fluoro-4-(6-(2-methyl-2H-tetrazol-5-yl)pyridin-3-yl)phenyl)-2-oxooxazolidin-5-yl)methoxy)-3-hydroxypropan-2-yl dihydrogen phosphate and, 3-((3-(3-fluoro-4-(6-(2-methyl-2H-tetrazol-5-yl)pyridin-3-yl)phenyl)-2-oxooxazolidin-5-yl)methoxy)-2-hydroxypropyl dihydrogen phosphate;

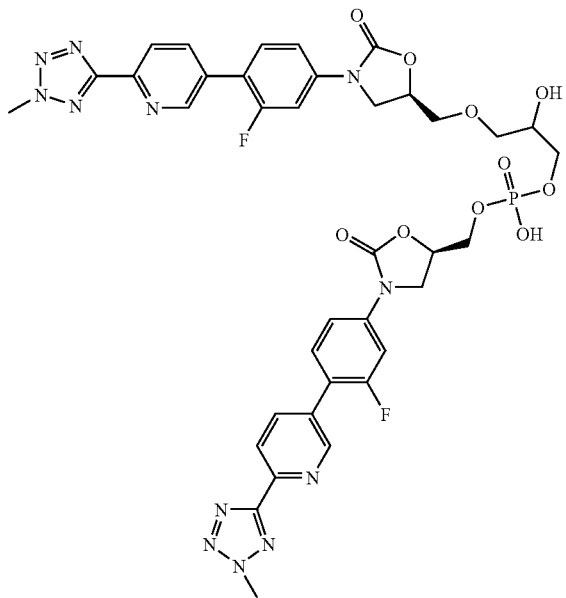 [SMILES: Cn1nnc(-c2ccc(-c3ccc(N4C[C@H](COCC(O)COP(=O)(O)OC[C@H]5CN(c6ccc(-c7ccc(-c8nnn(C)n8)nc7)c(F)c6)C(=O)O5)OC4=O)cc3F)cn2)n1]

(hereinafter "one of the OA-700 mixed di ester") i.e., 3-{[(5R)-3-{3-fluoro-4-[6-(2-methyl-2H-tetrazol-5-yl)pyridin-3-yl]phenyl}-2-oxo-1,3-oxazolidin-5-yl]methoxy}-2-hydroxypropyl [(5R)-3-{3-fluoro-4-[6-(2-methyl-2H-tetrazol-5-yl)pyridin-3-yl]phenyl}-2-oxo-1,3-oxazolidin-5-yl]methyl hydrogen phosphate; and/or

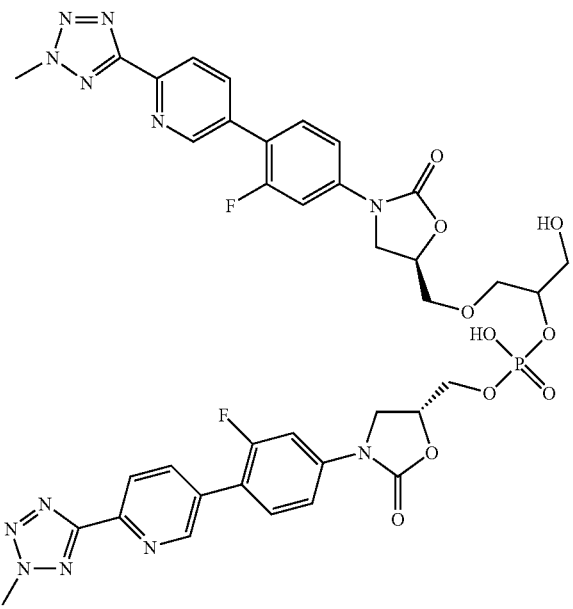 [SMILES: Cn1nnc(-c2ccc(-c3ccc(N4C[C@H](COCC(CO)OP(=O)(O)OC[C@H]5CN(c6ccc(-c7ccc(-c8nnn(C)n8)nc7)c(F)c6)C(=O)O5)OC4=O)cc3F)cn2)n1]

(hereinafter "another of the OA-700 mixed di ester") i.e., 2-{[(5R)-3-{3-fluoro-4-[6-(2-methyl-2H-tetrazol-5-yl)pyridin-3-yl]phenyl}-2-oxo-1,3-oxazolidin-5-yl]methoxy}-1-hydroxyethyl [(5R)-3-{3-fluoro-4-[6-(2-methyl-2H-tetrazol-5-yl)pyridin-3-yl]phenyl}-2-oxo-1,3-oxazolidin-5-yl] methyl hydrogen phosphate.

Those skilled in the art will appreciate that various isotopically-substituted variants (through, e.g., substitution of deuterium for hydrogen, $^{13}C$ for carbon, $^{15}N$ for nitrogen, or $^{32}P$ for phosphorus) can also be readily produced. All such variants are contemplated within the scope of this disclosure.

In various embodiments, the purified crystallized free acid disclosed herein can be used alone, in combination with other compounds disclosed herein, or in combination with one or more other agents active in the therapeutic areas described herein.

In another aspect, the present disclosure relates to a pharmaceutical composition comprising one or more physiologically acceptable surface active agents, additional carriers, diluents, excipients, smoothing agents, suspension agents, film forming substances, and coating assistants, or a combination thereof; and a composition disclosed herein. Acceptable additional carriers or diluents for therapeutic use are well known in the pharmaceutical art, and are described, for example, in Remington's Pharmaceutical Sciences, 18th Ed., Mack Publishing Co., Easton, Pa. (1990), which is incorporated herein by reference in its entirety. Preservatives, stabilizers, dyes, sweeteners, fragrances, flavoring agents, and the like may be provided in the pharmaceutical composition. For example, sodium benzoate, ascorbic acid and esters of p-hydroxybenzoic acid may be added as preservatives. In addition, antioxidants and suspending agents may be used. In various embodiments, alcohols, esters, sulfated aliphatic alcohols, and the like may be used as surface active agents; sucrose, glucose, lactose, starch, microcrystalline cellulose, crystallized cellulose, mannitol, light anhydrous silicate, magnesium aluminate, magnesium metasilicate aluminate, synthetic aluminum silicate, calcium carbonate, sodium acid carbonate, calcium hydrogen phosphate, calcium carboxymethyl cellulose, and the like may be used as excipients; magnesium stearate, talc, hardened oil and the like may be used as smoothing agents; coconut oil, olive oil, sesame oil, peanut oil, soya may be used as suspension agents or lubricants; cellulose acetate phthalate as a derivative of a carbohydrate such as cellulose or sugar, or methylacetate-methacrylate copolymer as a derivative of polyvinyl may be used as suspension agents; and plasticizers such as ester phthalates and the like may be used as suspension agents.

The term "pharmaceutical composition" refers to a mixture of a compound disclosed herein with other chemical components, such as diluents or additional carriers. The pharmaceutical composition facilitates administration of the compound to an organism. Multiple techniques of administering a pharmaceutical composition exist in the art including, but not limited to, oral, injection, aerosol, parenteral, and topical administration. Pharmaceutical compositions can also be obtained by reacting the free acid with inorganic or organic bases such as sodium hydroxide or magnesium hydroxide. In some embodiments, pharmaceutically acceptable salts of the compounds disclosed herein (e.g., as made in situ during the manufacture of an intravenous formulation) are provided. In some embodiments, sodium hydroxide is used to prepare a lyophilized powder the formulation that comprises a salt of the free acid, which is produced in situ.

The term "carrier" refers to a chemical compound that facilitates the incorporation of a compound into cells or tissues.

The term "diluent" refers to chemical compounds diluted in water that will dissolve the composition of interest as well as stabilize the biologically active form of the compound. Salts dissolved in buffered solutions are utilized as diluents in the art. One commonly used buffered solution is phosphate buffered saline because it mimics the salt conditions of human blood. Since buffer salts can control the pH of a solution at low concentrations, a buffered diluent rarely modifies the biological activity of a compound. As used herein, an "excipient" refers to an inert substance that is added to a composition to provide, without limitation, bulk, consistency, stability, binding ability, lubrication, disintegrating ability, etc., to the composition. A "diluent" is a type of excipient.

The term "physiologically acceptable" refers to a carrier or diluent that does not abrogate the biological activity and properties of the compound.

The pharmaceutical compounds described herein can be administered to a human patient per se, or in pharmaceutical compositions where they are mixed with other active ingredients, as in combination therapy, or suitable carriers or excipient(s). Techniques for formulation and administration of the compounds of the instant application may be found in "Remington's Pharmaceutical Sciences," Mack Publishing Co., Easton, Pa., 18th edition, 1990.

Suitable routes of administration may, for example, include oral, rectal, transmucosal, topical, or intestinal administration; parenteral delivery, including intramuscular, subcutaneous, intravenous, intramedullary injections, as well as intrathecal, direct intraventricular, intraperitoneal, intranasal, or intraocular injections. The compound can also be administered in sustained or controlled release dosage forms, including depot injections, osmotic pumps, pills, transdermal (including electrotransport) patches, and the like, for prolonged and/or timed, pulsed administration at a predetermined rate.

The pharmaceutical compositions of the present invention may be manufactured in a manner that is itself known, e.g., by means of conventional mixing, dissolving, granulating, dragee-making, levigating, emulsifying, encapsulating, entrapping or tabletting processes.

Pharmaceutical compositions may be formulated in any conventional manner using one or more physiologically acceptable carriers comprising excipients and auxiliaries which facilitate processing of the active compounds into preparations which can be used pharmaceutically. Proper formulation is dependent upon the route of administration chosen. Any of the well-known techniques, diluents, carriers, and excipients may be used as suitable and as understood in the art; e.g., in Remington's Pharmaceutical Sciences, above.

Injectables can be prepared in conventional forms, either as liquid solutions or suspensions, solid forms suitable for solution or suspension in liquid prior to injection, or as emulsions. Suitable excipients are, for example, water, saline, dextrose, mannitol, lactose, lecithin, albumin, sodium glutamate, cysteine hydrochloride, and the like. In addition, if desired, the injectable pharmaceutical compositions may contain minor amounts of nontoxic auxiliary substances, such as wetting agents, pH buffering agents, and the like. Physiologically compatible buffers include, but are not limited to, Hanks's solution, Ringer's solution, or physiological saline buffer. If desired, absorption enhancing preparations may be utilized.

For transmucosal administration, penetrants appropriate to the barrier to be permeated may be used in the formulation.

Pharmaceutical formulations for parenteral administration, e.g., by bolus injection or continuous infusion, include aqueous solutions of the active compounds in water-soluble form. Additionally, suspensions of the active compounds may be prepared as appropriate oily injection suspensions. Aqueous injection suspensions may contain substances which increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

For oral administration, the composition can be formulated readily by combining the compositions of interest with pharmaceutically acceptable carriers well known in the art. Such carriers, which may be used in addition to the cationic polymeric carrier, enable the compositions of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP), e.g., Povidone. If desired, disintegrating agents may be added, such as the cross-linked polyvinylpyrrolidone (e.g. Crospovidone), agar, or alginic acid or a salt thereof such as sodium alginate. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the composition can be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Further disclosed herein are various pharmaceutical compositions well known in the pharmaceutical art for uses that include intraocular, intranasal, and intraauricular delivery. Suitable penetrants for these uses are generally known in the art. Such suitable pharmaceutical formulations are most often and preferably formulated to be sterile, isotonic and buffered for stability and comfort. Pharmaceutical compositions for intranasal delivery may also include drops and sprays often prepared to simulate in many respects nasal secretions to ensure maintenance of normal ciliary action. As disclosed in Remington's Pharmaceutical Sciences, 18th Ed., Mack Publishing Co., Easton, Pa. (1990), which is incorporated herein by reference in its entirety, and well-known to those skilled in the art, suitable formulations are most often and preferably isotonic, slightly buffered to maintain a pH of 5.5 to 6.5, and most often and preferably include antimicrobial preservatives and appropriate drug stabilizers. Pharmaceutical formulations for intraauricular delivery include suspensions and ointments for topical application in the ear. Common solvents for such aural formulations include glycerin and water.

The compositions may also be formulated in rectal compositions such as suppositories or retention enemas, e.g., containing conventional suppository bases such as cocoa butter or other glycerides.

In addition to the formulations described previously, the compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For hydrophobic compounds, a suitable pharmaceutical carrier may be a cosolvent system comprising benzyl alcohol, a nonpolar surfactant, a water-miscible organic polymer, and an aqueous phase. A common cosolvent system used is the VPD co-solvent system, which is a solution of 3% w/v benzyl alcohol, 8% w/v of the nonpolar surfactant Polysorbate 80™, and 65% w/v polyethylene glycol 300, made up to volume in absolute ethanol. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of POLYSORBATE 80™; the fraction size of polyethylene glycol may be varied; other biocompatible polymers may replace polyethylene glycol, e.g., polyvinyl pyrrolidone; and other sugars or polysaccharides may substitute for dextrose.

Methods for treating bacterial infections may include administering a therapeutically effective amount of the therapeutic compounds as described herein. Treating a bacterial infection may also include prophylactically administering the therapeutic compounds to prevent infection or the spread of an infection in a subject at imminent risk of infection, such as a subject receiving or about to undergo surgery, an immunocompromised subject, or subject otherwise at risk of an infection if the compound was not administered. The compounds show inhibitory activity against a broad spectrum of bacteria, against methicillin resistant Staphylococcus aureus (MRSA) and vancomycin resistant Enterococci (VRE) and have excellent relative antibiotic activity with a relatively low concentration thereof or in vivo. Further, the compounds of the present invention may exert potent antibacterial activity versus various human and animal pathogens, including Gram-positive bacteria such as Staphylococi, Enterococci and Streptococi, anaerobic microorganisms such as Bacteroides and Clostridia, and acid-resistant microorganisms such as Mycobacterium tuberculosis and Mycobacterium avium. In an embodiment, the bacterial infection that may be treated or ameliorated is MRSA.

The compositions or pharmaceutical compositions described herein may be administered to the subject by any suitable means. Non-limiting examples of methods of administration include, among others, (a) administration though oral pathways, which administration includes administration in capsule, tablet, granule, spray, syrup, or other such forms; (b) administration through non-oral pathways such as rectal, vaginal, intraurethral, intraocular, intranasal, or intraauricular, which administration includes administration as an aqueous suspension, an oily preparation or the like or as a drip, spray, suppository, salve, ointment or the like; (c) administration via injection, subcutaneously, intraperitoneally, intravenously, intramuscularly, intradermally, intraorbitally, intracapsularly, intraspinally, intrasternally, or the like, including infusion pump delivery; as well as (d) administration topically; as deemed appropriate by those of skill in the art for bringing the active compound into contact with living tissue.

Pharmaceutical compositions suitable for administration include compositions where the active ingredients are contained in an amount effective to achieve its intended purpose. The therapeutically effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize. More specifically, a therapeutically effective amount means an amount of compound effective to prevent, alleviate or ameliorate symptoms of disease or prolong the survival of the subject being treated. Determination of a therapeutically effective amount is well within the capability of those skilled in the art, especially in light of the detailed disclosure provided herein.

As will be readily apparent to one skilled in the art, the useful in vivo dosage to be administered and the particular mode of administration will vary depending upon the age, weight and mammalian species treated, the particular compounds employed, and the specific use for which these compounds are employed. The determination of effective dosage levels, that is the dosage levels necessary to achieve the desired result, can be accomplished by one skilled in the art using routine pharmacological methods. Typically, human clinical applications of products are commenced at lower dosage levels, with dosage level being increased until the desired effect is achieved. Alternatively, acceptable in vitro studies can be used to establish useful doses and routes of administration of the compositions identified by the present methods using established pharmacological methods.

In non-human animal studies, applications of potential products are commenced at higher dosage levels, with dosage being decreased until the desired effect is no longer achieved adverse side effects disappear. The dosage may range broadly, depending upon the desired effects and the therapeutic indication. Typically, dosages may be about 10 microgram/kg to about 100 mg/kg body weight, preferably about 100 microgram/kg to about 10 mg/kg body weight. Alternatively dosages may be based and calculated upon the surface area of the patient, as understood by those of skill in the art.

The exact formulation, route of administration and dosage for the pharmaceutical compositions of the present invention can be chosen by the individual physician in view of the patient's condition. (See e.g., Fingl et al. 1975, in "The Pharmacological Basis of Therapeutics", which is hereby incorporated herein by reference in its entirety, with particular reference to Ch. 1, p. 1). Typically, the dose range of the composition administered to the patient can be from about 0.5 to about 1000 mg/kg of the patient's body weight. The dosage may be a single one or a series of two or more given in the course of one or more days, as is needed by the patient. In instances where human dosages for compounds have been established for at least some condition, the present invention will use those same dosages, or dosages that are about 0.1% to about 500%, more preferably about 25% to about 250% of the established human dosage. Where no human dosage is established, as will be the case for newly-discovered pharmaceutical compositions, a suitable human dosage can be inferred from $ED_{50}$ or $ID_{50}$ values, or other appropriate values derived from in vitro or in vivo studies, as qualified by toxicity studies and efficacy studies in animals.

It should be noted that the attending physician would know how to and when to terminate, interrupt, or adjust administration due to toxicity or organ dysfunctions. Conversely, the attending physician would also know to adjust treatment to higher levels if the clinical response were not adequate (precluding toxicity). The magnitude of an administrated dose in the management of the disorder of interest will vary with the severity of the condition to be treated and to the route of administration. The severity of the condition may, for example, be evaluated, in part, by standard prognostic evaluation methods. Further, the dose and perhaps dose frequency will also vary according to the age, body weight, and response of the individual patient. A program comparable to that discussed above may be used in veterinary medicine.

Although the exact dosage will be determined on a drug-by-drug basis, in most cases, some generalizations regarding the dosage can be made. The daily dosage regimen for an adult human patient may be, for example, an oral dose of about 0.1 mg to 2000 mg of each active ingredient, preferably about 1 mg to about 500 mg, e.g. 5 to 200 mg. In other embodiments, an intravenous, subcutaneous, or intramuscular dose of each active ingredient of about 0.01 mg to about 100 mg, preferably about 0.1 mg to about 60 mg, e.g. about 1 to about 40 mg is used. In cases of administration of a pharmaceutically acceptable salt, dosages may be calculated as the free base. In some embodiments, the composition is administered 1 to 4 times per day. Alternatively the compositions of the invention may be administered by continuous intravenous infusion, preferably at a dose of each active ingredient up to about 1000 mg per day. As will be understood by those of skill in the art, in certain situations it may be necessary to administer the compounds disclosed herein in amounts that exceed, or even far exceed, the above-stated, preferred dosage range in order to effectively and aggressively treat particularly aggressive diseases or infections. In some embodiments, the compounds will be administered for a period of continuous therapy, for example for a week or more, or for months or years.

Dosage amount and interval may be adjusted individually to provide plasma levels of the active moiety which are sufficient to maintain the modulating effects, or minimal effective concentration (MEC). The MEC will vary for each compound but can be estimated from in vitro data. Dosages necessary to achieve the MEC will depend on individual characteristics and route of administration. However, HPLC assays or bioassays can be used to determine plasma concentrations.

Dosage intervals can also be determined using MEC value. Compositions should be administered using a regimen which maintains plasma levels above the MEC for 10-90% of the time, preferably between 30-90% and most preferably between 50-90%.

In cases of local administration or selective uptake, the effective local concentration of the drug may not be related to plasma concentration.

The amount of composition administered may be dependent on the subject being treated, on the subject's weight, the severity of the infection, the manner of administration and the judgment of the prescribing physician.

Compositions disclosed herein can be evaluated for efficacy and toxicity using known methods. For example, the toxicology of the compound may be established by determining in vitro toxicity towards a cell line, such as a mammalian, and preferably human, cell line. The results of such studies are often predictive of toxicity in animals, such as mammals, or more specifically, humans. Alternatively, the toxicity of particular compounds in an animal model, such as mice, rats, rabbits, or monkeys, may be determined using known methods. The efficacy of a particular compound may be established using several recognized methods, such as in vitro methods, animal models, or human clinical trials. Recognized in vitro models exist for nearly every class of condition. Similarly, acceptable animal models may be used to establish efficacy of chemicals to treat such conditions. When selecting a model to determine efficacy, the skilled artisan can be guided by the state of the art to choose an appropriate model, dose, and route of administration, and regime. Of course, human clinical trials can also be used to determine the efficacy of a compound in humans.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. The pack or dispenser may also be accompanied with a notice associated with the container in form prescribed by a governmental agency regulating the manufacture, use, or sale of pharmaceuticals, which notice is reflective of approval by the agency of the form of the drug for human or veterinary administration. Such notice, for example, may be the labeling approved by the U.S. Food and Drug Administration for prescription drugs, or the approved product insert. Compositions comprising a compound of the invention formulated in a compatible pharmaceutical carrier may also be prepared, placed in an appropriate container, and labeled for treatment of an indicated condition.

A. EXAMPLES

1. Instrumentation

Raman microscopy was performed on a Renishaw System 1000, with stabilized diode laser 385 nm excitation and a NIR enhanced Peltier-cooled charge coupled device camera as detector. Measurements were carried out with 50× or a long working distance 20× objective over a frequency range of 2000-100 $cm^{-1}$.

FT-Raman spectra were obtained on a Bruker RFS100 spectrometer with Nd:YAG 1064 nm excitation, 100 mW laser power, and a Ge detector. Sixty-four scans were recorded over the range 25-3500 $cm^{-1}$, at 2 $cm^{-1}$ resolution.

Bruker D8; Bragg-Brentano, reflection geometry; Copper K(alpha) radiation, 40 kV/40 mA; variable divergence slit; LynxEye detector with 3° window; step size, 0.02-° 2; step time, 37 s. The samples were rotated (0.5 rps) during the measurement.

Sample preparation: The samples were generally prepared without any special treatment other than the application of slight pressure to get a flat surface. Silicon single crystal sample holder types: a) standard holder for polymorph screening, 0.1 mm deep, less than 20 mg sample required; b) 0.5 mm deep, 12 mm cavity diameter, ca. 40 mg required; c) 1.0 mm deep, 12 mm cavity diameter, ca. 80 mg required. Normally samples were measured uncovered. Kapton foil or PMMA "dome" covers are always indicated on the diffractogram with the sample identification.

2. Preparation of Crystalline Free Acid 1 (R=PO(OH)$_2$)

Example 1

Figure 3:
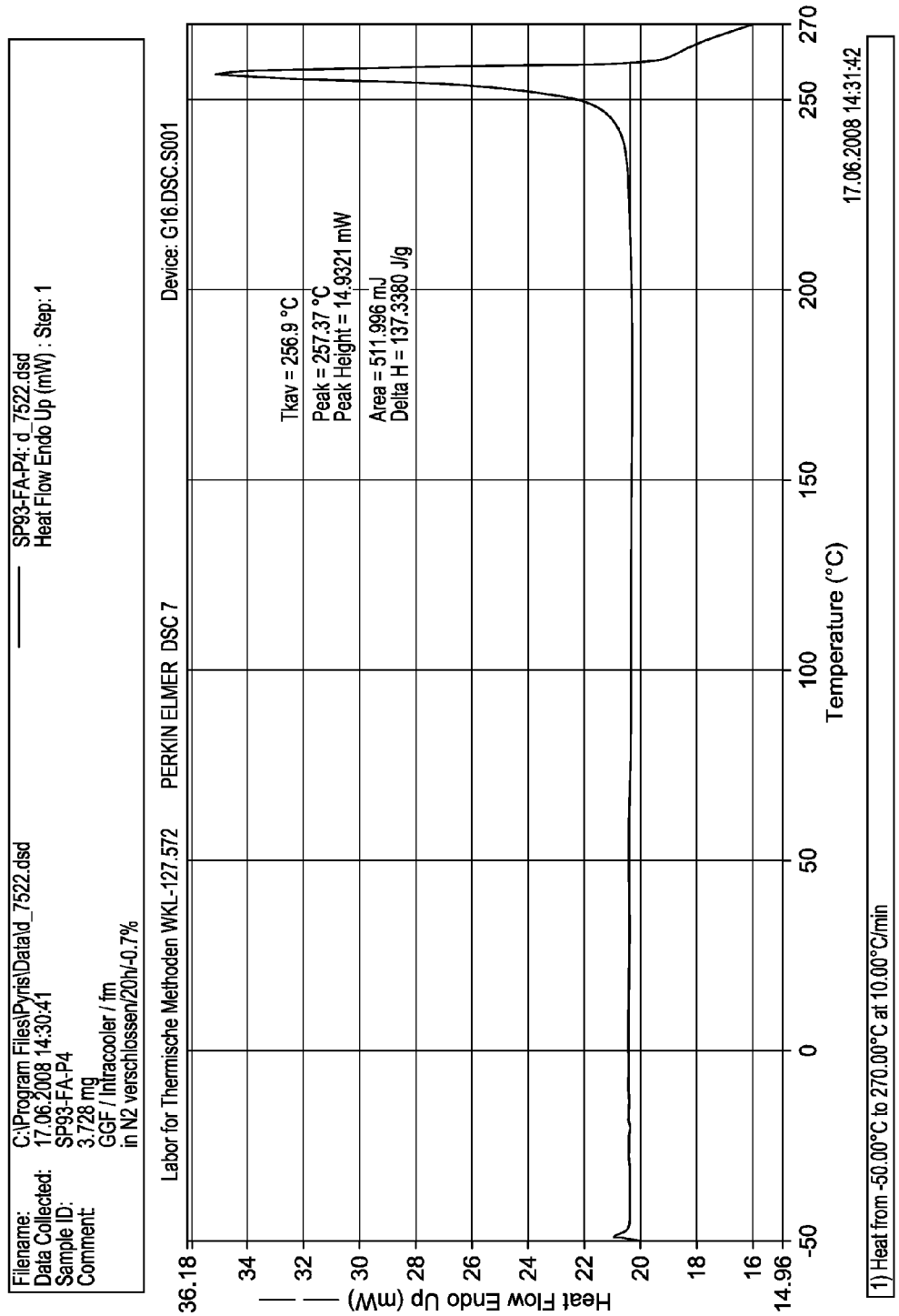
FIG. 3 shows the differential scanning calorimetry (DSC) thermogram of crystalline 1 (R=PO(OH)$_2$).
Figures 1, 4:
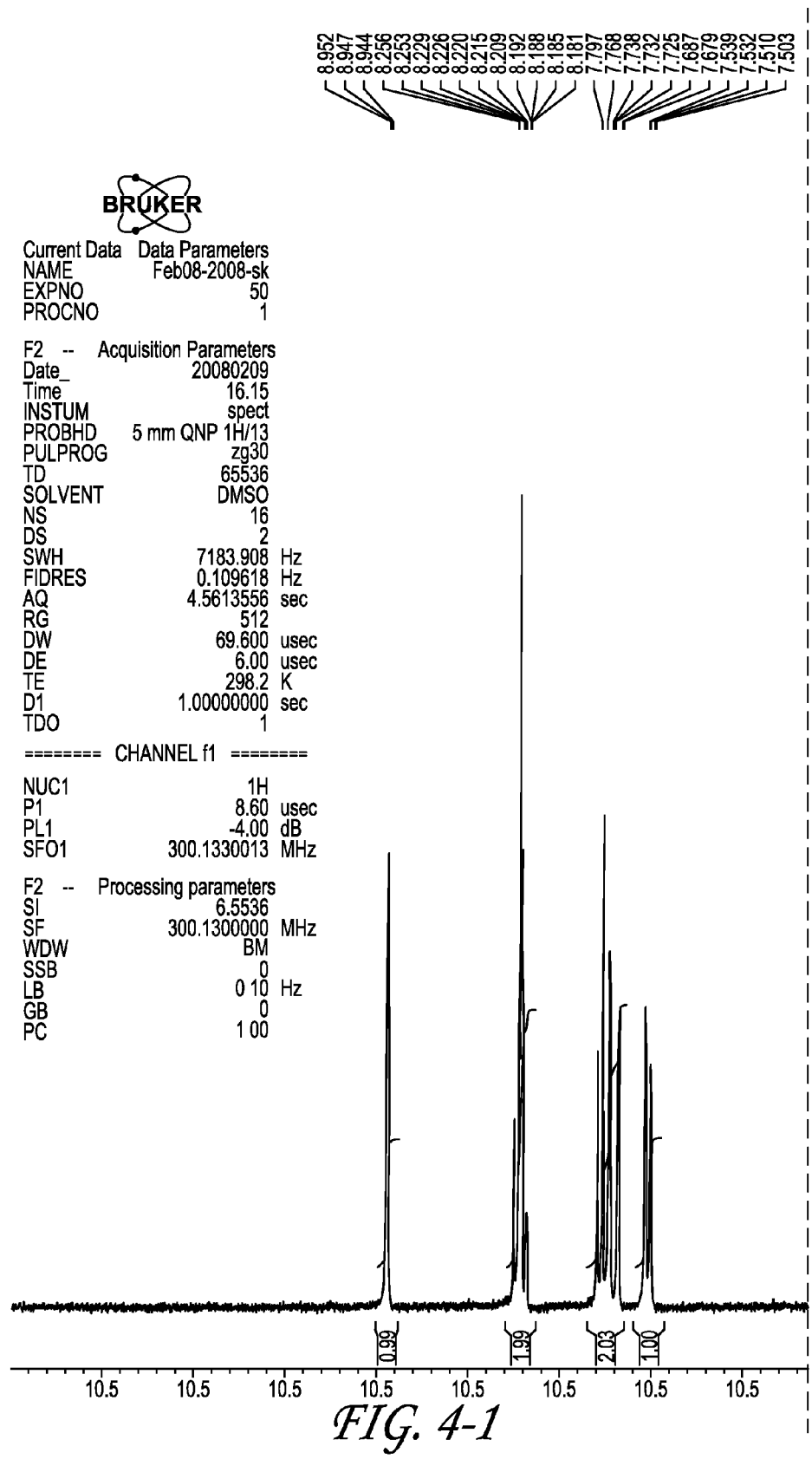
FIG. 4 shows the $^1$H NMR spectrum of 1 (R=PO(OH)$_2$).
Figures 2, 4:
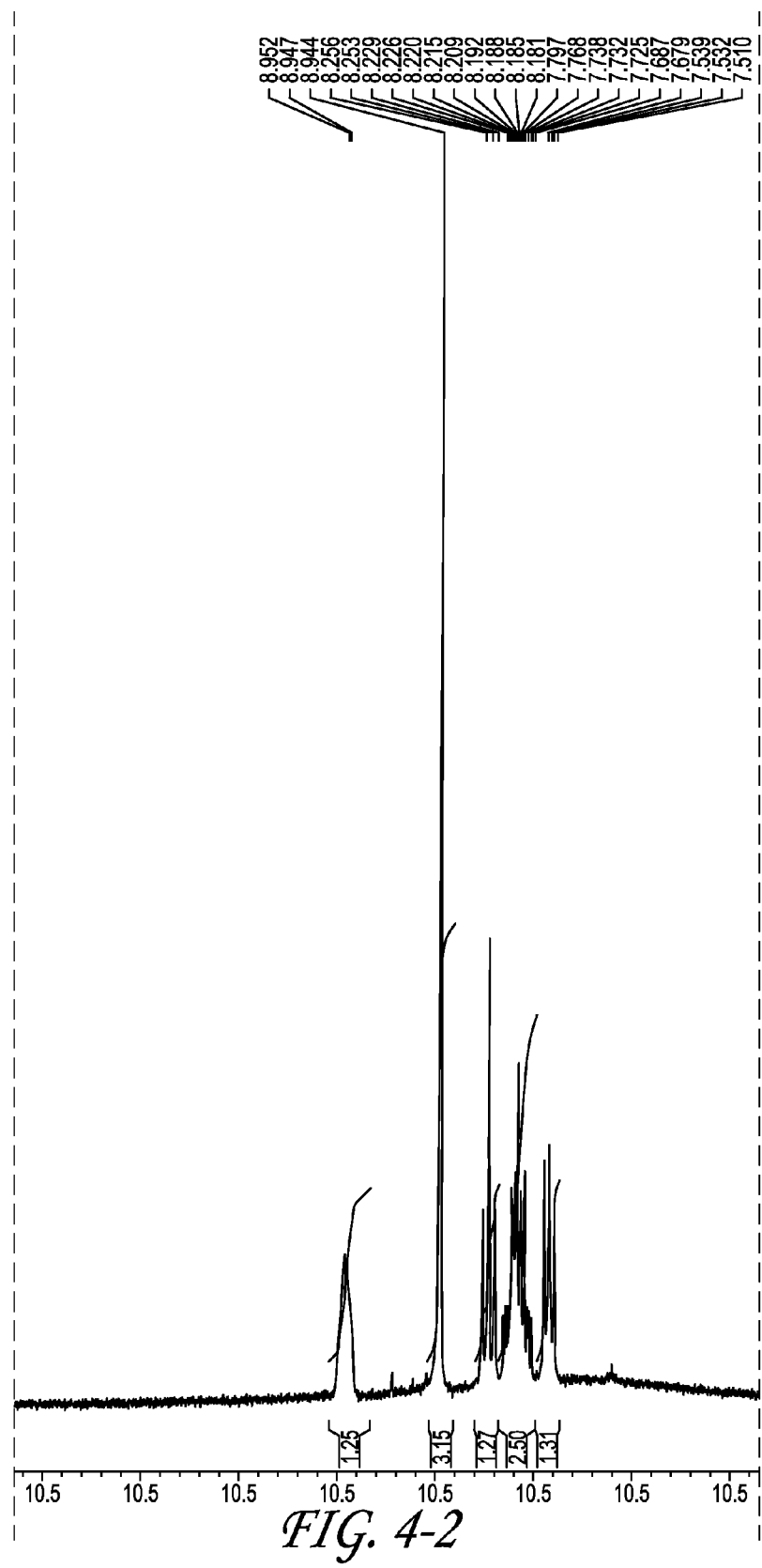
Figures 3, 4:
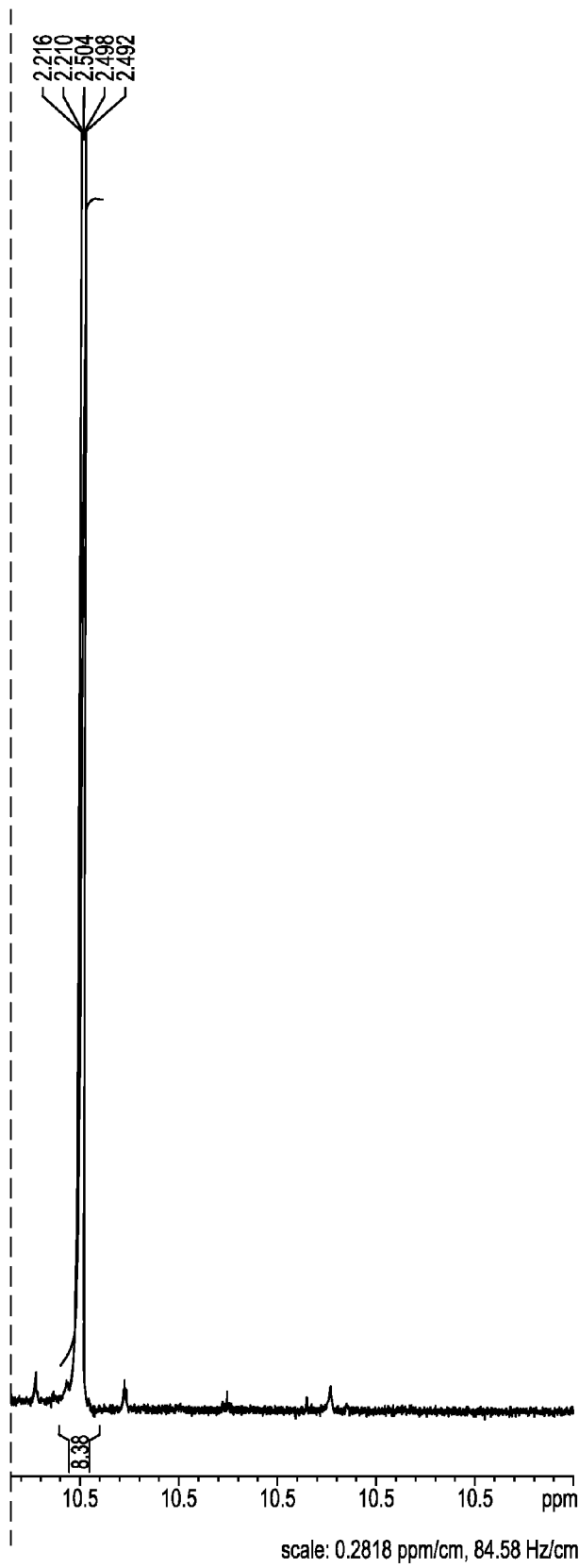
Figure 5:
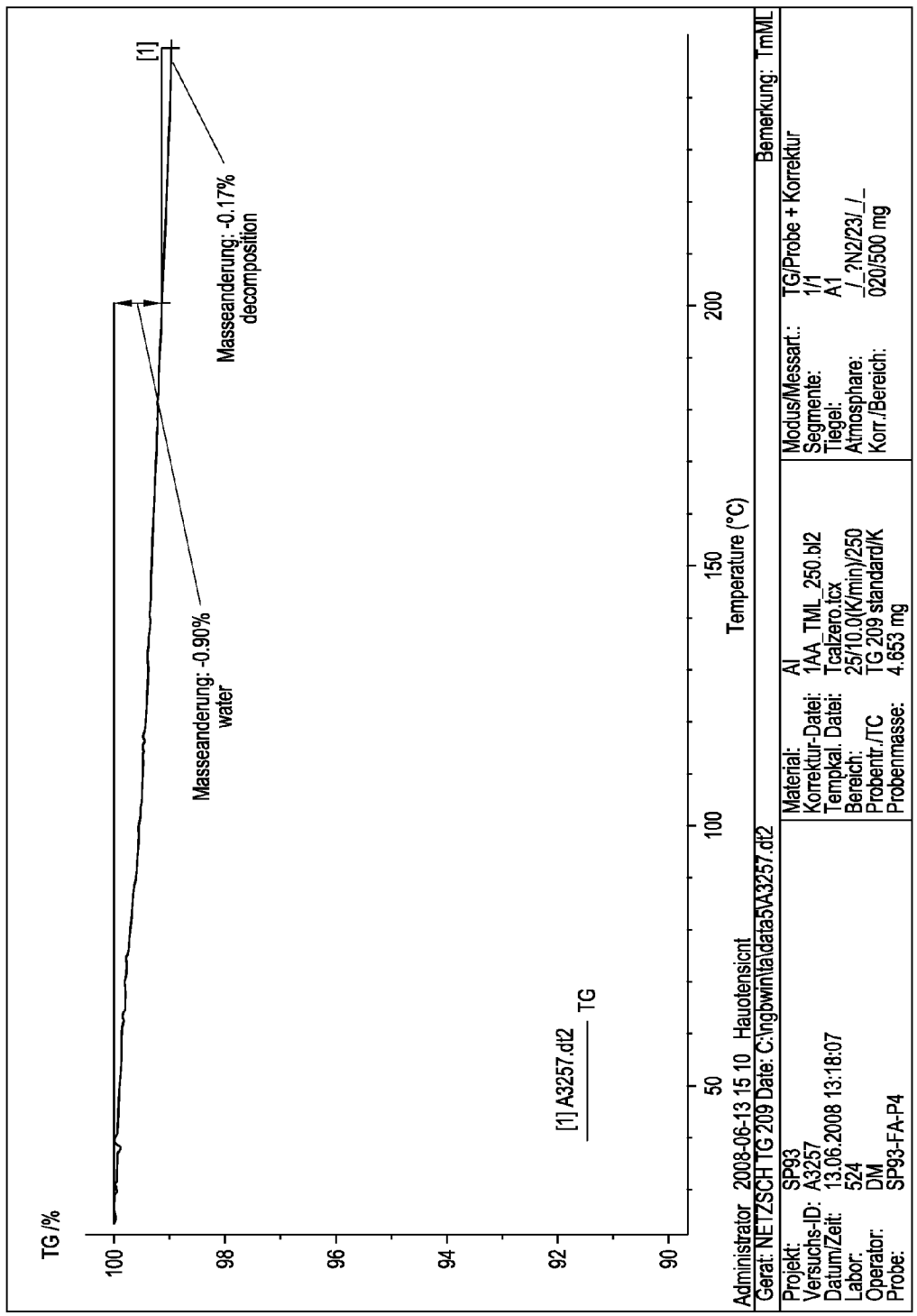
FIG. 5 depicts the TG-FTIR diagram of crystalline 1 (R=PO(OH)$_2$).
Figure 6:
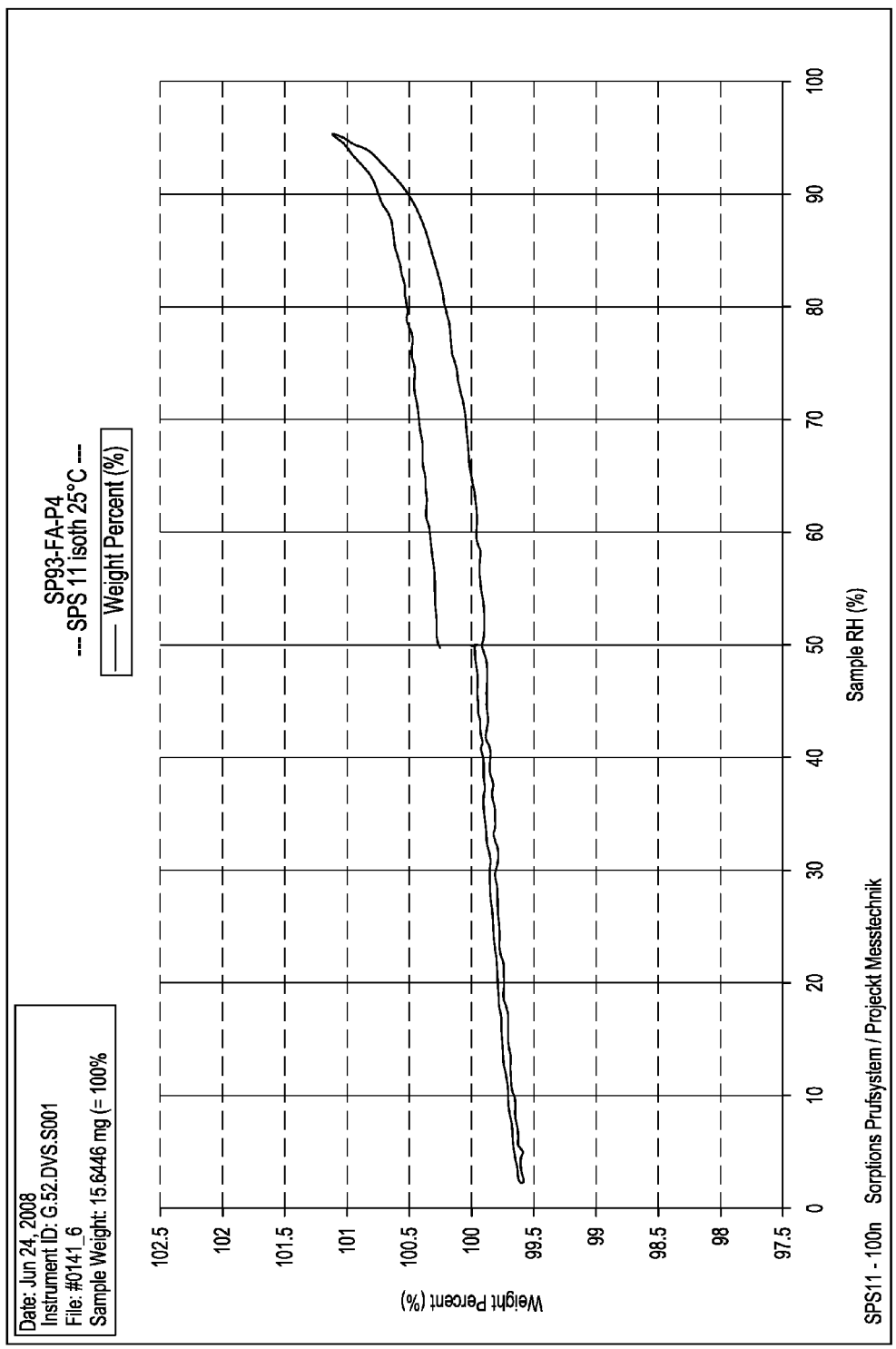
FIG. 6 is a diagram showing the dynamic vapor sorption (DVS) behavior of crystalline 1 (R=PO(OH)$_2$).

A solution of 1 (R=PO(ONa)$_2$) was prepared in H$_2$O and 1 M HCl added to give a fine suspension, which, after addition of tetrahydrofuran (THF), was stirred and filtered. The resulting crystalline solid 1 (R=PO(OH)$_2$) was dried in vacuum, and characterized by FT-Raman (FTR) (FIG. 1), X-ray powder diffraction (XRPD, Malvern Mastersizer) (FIG. 2), thermogravimetry-Fourier transform infrared spectroscopy (TG-FTIR), and differential scanning calorimetry (DSC). DSC measurement showed a melting point at 256.9° C. followed by a decomposition of the sample (FIG. 3).

Example 2

To 1 (R=PO(ONa)$_2$) (2 g) dissolved in 10 mL H$_2$O was slowly added HCl (6 mL; 1 M) to yield a fine suspension of a light yellow solid. After addition of a further 5 mL H$_2$O and 20 mL THF the suspension was filtered and dried in vacuum.

Example 3

To 1 (R=PO(ONa)$_2$) (2 g) dissolved in 10 mL H$_2$O was slowly added HCl (8 mL; 1 M) to give a fine suspension of a light yellow solid, to which a further 25 mL H$_2$O were added. The solid was filtered, washed with 10 mL 0.1 M HCl and 100 mL water and dried in vacuum.

Example 4

To 1 (R=PO(ONa)$_2$) (5 g) dissolved in 30 mL water was added 15 mL HCl (1 M) and 30 mL of THF to produce a light yellow suspension, which was stirred 30 min at room temperature and filtered. The resulting solid was suspended in 150 mL water and stirred 60 min at room temperature. Then 50 mL THF were added and the suspension was stirred 18 h. The suspension was filtered and the solid was washed with 10 mL HCl (0.1 M) and 100 mL water and dried in vacuum (15 h).

Example 5

To 1 (R=PO(ONa)$_2$) (2 g) dissolved in 15 mL water was slowly added HCl (6 mL; 1 M) to give a light yellow suspension. After addition of 20 mL THF and 60 mL water the suspension was stirred 18 hours, filtered, and the solid was stirred again in 6 mL HCl (1 M) for 15 min. Afterwards the suspension was filtered and the solid was dried in vacuum.

Example 6

To 1 (R=PO(ONa)$_2$) (3 g) dissolved in 35 mL water was added HCl (9 mL; 1 M) to yield a light yellow suspension. After addition of 20 mL THF the suspension was stirred 30 min at room temperature and then filtered. The resulting solid was washed with 20 mL HCl (0.1 M) and water and dried in vacuum.

Example 7

Solid dihydrogen phosphate is added to a volume of DMSO or N-methylpyrrolidinone at about 50° C. until no more salt dissolves. The solution containing suspended salt is then heated further just until the remaining solid dissolves, and the solution filtered while hot and allowed to cool undisturbed, when it deposits crystals of the dihydrogen phosphate.

Example 8

A solution of the dihydrogen phosphate is prepared in DMSO or N-methylpyrrolidinone and filtered. To the filtered solution is added ethanol with stifling until the solution becomes cloudy. Stirring is then discontinued, and a layer of ethanol carefully placed on top of the cloudy solution, which is allowed to sit undisturbed, when it deposits crystals of the dihydrogen phosphate.

Example 9

A solution of the dihydrogen phosphate is prepared in DMSO or N-methylpyrrolidinone and filtered. The filtered solution is then exposed to vapor of ethanol, for example by placing an open container of the solution and an open container of ethanol together in a sealed vessel such that the two containers share a common headspace inside the vessel. On standing the container with the solution deposits crystals of the dihydrogen phosphate.

Example 10

A solution of a salt of the dihydrogen phosphate, such as the mono- or disodium phosphate, is prepared. Such a solution can be prepared by such methods as simply dissolving a sample of the solid disodium phosphate in water, or by adding the dihydrogen phosphate to an aqueous solution of a base sufficiently strong to substantially deprotonate the dihydrogen phosphate. Identification of an appropriate base is a routine matter for the practicing chemist. Typically the resulting solution of the salt of the dihydrogen phosphate is then filtered, and to the filtrate is added an acid to reprotonate the salt and induce crystallization of the dihydrogen phosphate. In a typical example, the dihydrogen phosphate is added to an aqueous solution containing NaOH or Na$_2$CO$_3$ to yield a solution of the disodium phosphate, to which after filtration is added aqueous or gaseous HCl to regenerate the dihydrogen phosphate, which deposits as crystals.

For pharmaceutical purposes it is advantageous to use pharmaceutically-acceptable acids and bases in this process, such as those compiled in Handbook of Pharmaceutical Salts Properties, Selection and Use. (P. Heinrich Stahl and Camille G. Wermuth, eds.) International Union of Pure and Applied Chemistry, Wiley-VCH 2002 and L. D. Bighley, S. M. Berge, D. C. Monkhouse, in "Encyclopedia of Pharmaceutical Technology'. Eds. J. Swarbrick and J. C. Boylan, Vol. 13, Marcel Dekker, Inc., New York, Basel, Hong Kong 1995, pp. 453-499 discusses such salts in detail.

As those skilled in the art will appreciate, elements of the methods above can be combined. For example, a solution of the dihydrogen phosphate in DMSO or N-methylpyrrolidinone can be prepared at one temperature, a second solvent such as ethanol added, and the resulting solution allowed to cool. Similarly, mixtures of solvents can be used instead of pure solvents, as is well-known to those skilled in crystallizing compounds. Furthermore, other solvents and mixtures thereof can also be used.

Elemental analysis for $C_{17}H_{16}FN_6O_6P$ (measured/calculated) C, 43.9 (44.8); H, 3.6 (3.7); N, 18.1 (18.4); O, 21.2 (22.1); F, 4.2 (4.2); P, 6.7 (6.8).

Example 11

The particle size was measured using a Malvern Mastersizer. The sampling instructions that were consistent with the instrument manufacturer's instructions were followed. The sample was prepared by suspending in 1-2 mL of deionized water and sonicating for 3 minutes.

Figure 10:
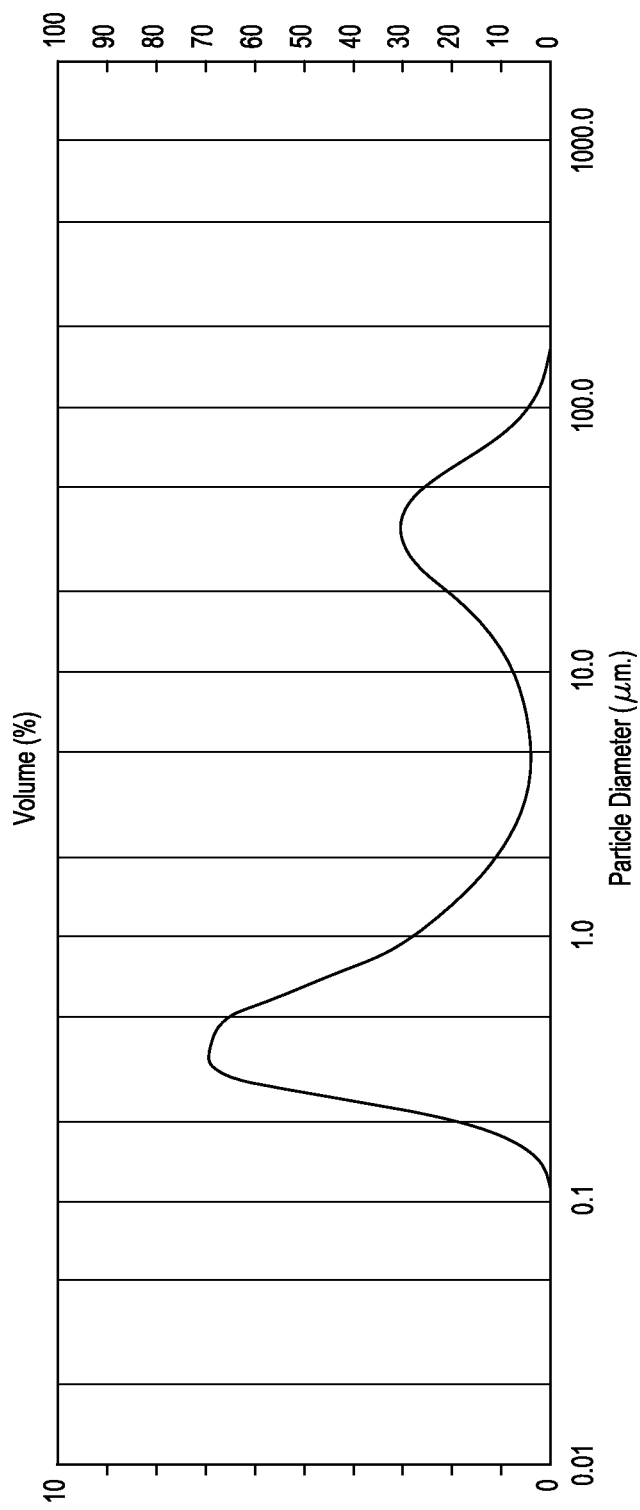
FIG. 10 is a representative particle size distribution of crystalline free acid without regard to controlling particle size distribution as also described herein.

An exemplary particle size distribution of crystalline material such as those described in Examples 1-10 above is set forth in FIG. 10 and Table 3 below:

TABLE 3

Typical Particle Size Distribution (uncontrolled process)

| Lot 02090054 | D10 (um) | D50 (um) | D90 (um) |
|---|---|---|---|
| Average | 0.28 | 0.79 | 44 |

Example 12

Particle-Size Adjustment Experimental

A 22-L reactor was charged with 1 M HCl (1.95 L, 2.2 equivalents) and ethanol (1.6 L, 4 volumes), and the solution was heated to 70° C. A separate 12-L reactor equipped with a gas bubbler to monitor gas evolution was charged with TR-701FA [0.4 kg, AMRI lot # DUG-AH-166(2)], water (2.8 L, 7 vol), and ethanol (0.4 L, 1 vol). The slurry was stirred at ambient temperature and 5 wt % aqueous $NaHCO_3$ was added via peristaltic pump over 30 minutes. No foaming was observed, however the gas evolution was vigorous as observed through the gas bubbler. Upon completion of the addition, the clear yellow solution was pH 6.6. The aqueous TR-701 solution was added via peristaltic pump to the ethanol/HCl solution over 90 minutes. Upon completion of the addition, the pH of the reaction mixture was 1.9 and the reaction mixture was cooled to 30° C. A sample of the slurry was withdrawn for analysis by optical microscopy. The slurry was filtered through a polypropylene filter cloth and the reactor and filter cake were rinsed with water (5 volumes) and acetone (5 volumes). The total filtration time including the washes was 12 minutes. The solids were dried under high vacuum at 50° C. to afford 391.7 g of reprecipitated TR-701FA (98% yield). Analysis by $^1H$ NMR was consistent with the assigned structure. HPLC analysis (Method A): 98.8% (AUC) $t_R$=5.2 min. The level of residual ethanol by $^1H$ NMR analysis was 0.03%, the water content was 0.15% by Karl Fischer titration, and the sodium content was 5 ppm.

Figure 11:
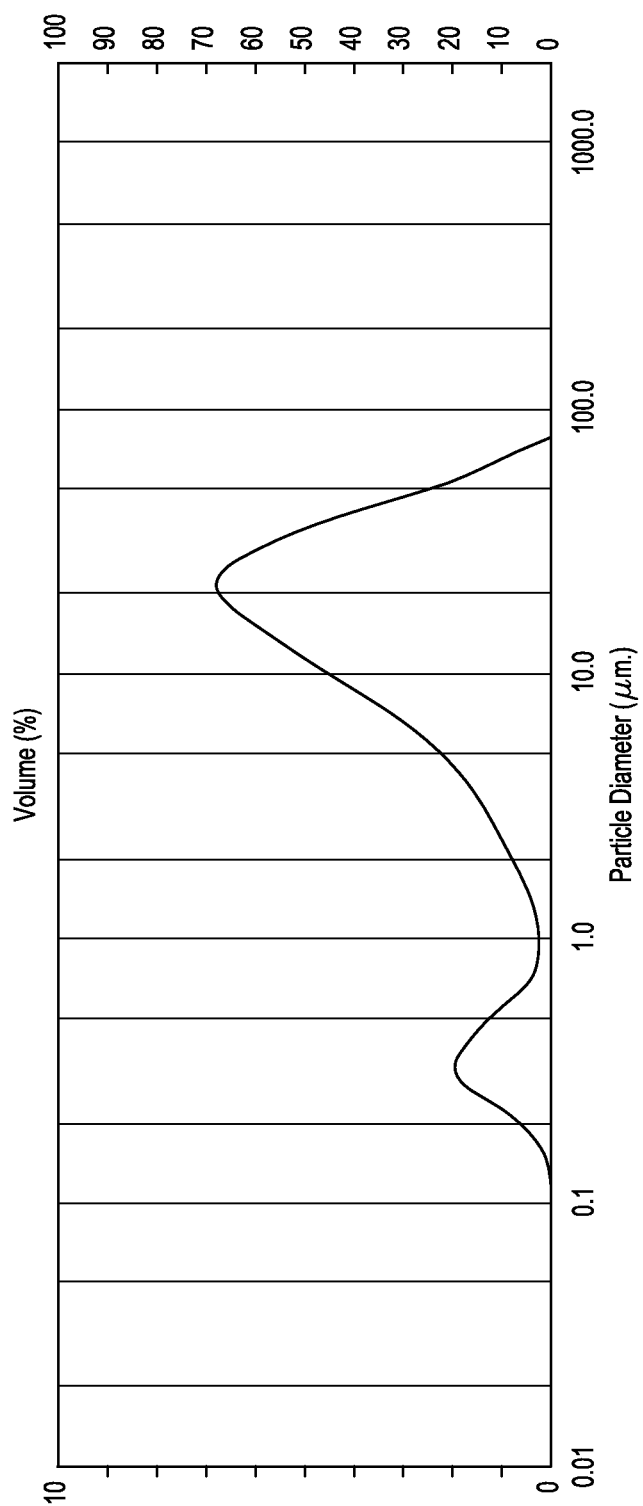
FIG. 11 is a representative particle size distribution of crystalline free acid made using laboratory processes to control particle size described herein.

The particle size was measured using a Malvern Mastersizer laser scattering microscopy. The sampling instructions that were consistent with the instrument manufacturer's instructions were followed. The sample was prepared by suspending in 1-2 mL of deionized water and sonicating for 3 minutes. The laser diffraction data is set forth in FIG. 11 and in Table 4 below.

TABLE 4

| Lot JAS-I-45 | D10 (um) | D50 (um) | D90 (um) |
|---|---|---|---|
| Average | 0.45 | 14.13 | 38.42 |

Figure 12:
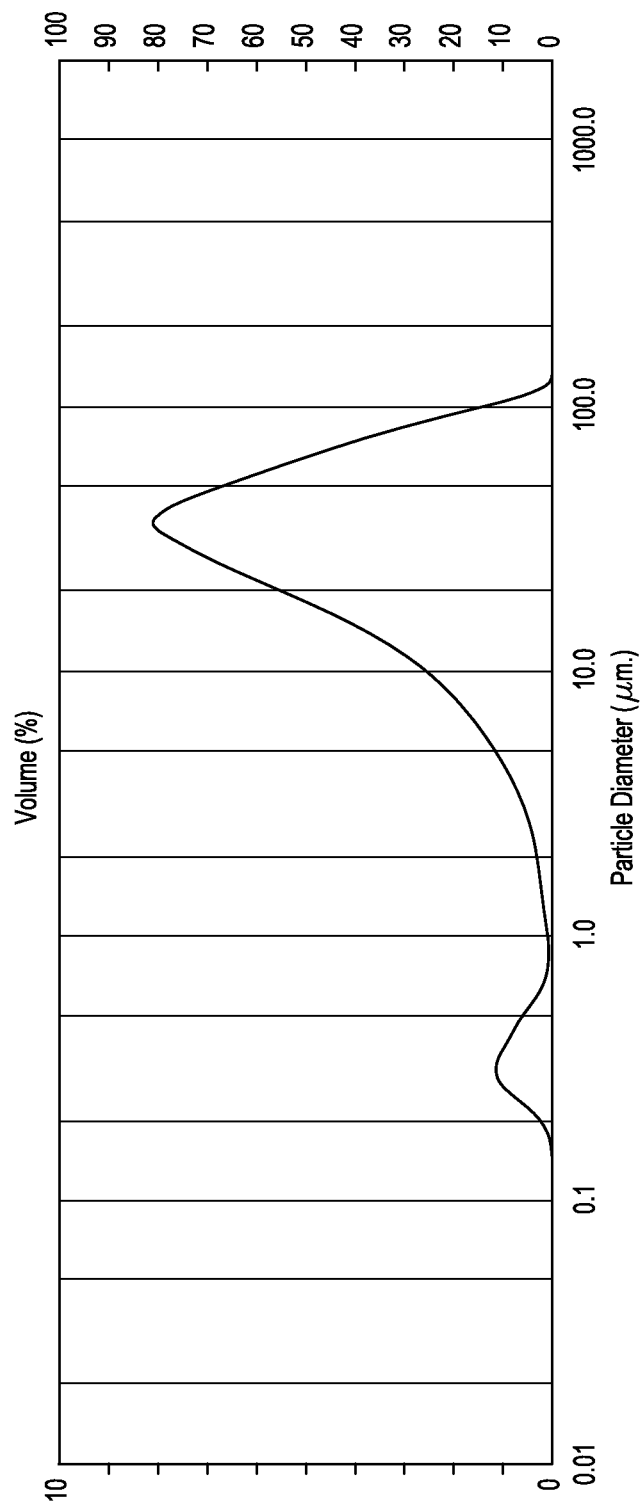
FIG. 12 is a representative particle size distribution of crystalline free acid made using scaled up manufacturing processes to control particle size described herein.

In another experiment, the typical particle size distribution using a controlled method, such as provided in this example, is set forth FIG. 12 and in Table 5 below:

TABLE 5

Typical Particle Size Distribution (using particle size control process)

| Lot 0209118 | D10 (μm) | D50 (μm) | D90 (μm) |
|---|---|---|---|
| Average | 3.3 | 27 | 66 |
| Range for Application | 1-5 | 1-40 | 45-80 |

The immediate release formulation and the intravenous formulation described in Examples 13-14 below were made using the crystalline free acid wherein the particle size was controlled.

Example 13

Immediate Release Formulation

The qualitative and quantitative formulation of immediate release (R)-3-(4-(2-(2-methyltetrazol-5-yl)pyridin-5-yl)-3-fluorophenyl)-5-hydroxymethyl oxazolidin-2-one dihydrogen phosphate 1 (R=$PO(OH)_2$) tablets ("Torezolid Phosphate Tablets"), 200 mg, is presented in Table 6. All components used in the manufacturing are listed with the quality standard, function, and weight percent of each individual component. The listing is inclusive of all materials used during the manufacture of the drug product whether or not they are present in the finished product.

TABLE 6

Composition of Torezolid Phosphate Tablets, 200 mg

| | | | 200 mg Tablet | |
|---|---|---|---|---|
| Ingredient | Quality Standard | Function | Weight (mg/unit) | % (w/w) |
| Torezolid Phosphate[1] | In-house | Active Ingredient | 200 | 50.0 |
| Microcrystalline Cellulose (Avicel PH-101) | NF | Diluent | 78.0 | 19.5 |
| Mannitol[2] (Mannogen ® EZ Spray Dried) | NF | Diluent | 78.0 | 19.5 |
| Povidone (Plasdone K-29/32) | NF | Binder | 16.0 | 4.0 |
| Crospovidone (Kollidon ® CL) | NF. | Disintegrant | 24.0 | 6.0 |
| Purified Water[2] | USP | Granulating Medium | — | — |
| Magnesium Stearate (HyQual ®) Vegetable Source | NF | Lubricant | 4.0 | 1.0 |
| Total Core Tablet Weight[1] | | | 400.0 | 100.0 |
| Opadry II Yellow | | Colored Film Coat | 14.0 | 3.4 |
| Purified Water[3] | USP | Film Coating Medium | — | — |
| Total Weight | | | 414.0 | 103.4 |

Abbreviations:
NF = National Formulary;
USP = United States Pharmacopeia
[1]The actual amount of torezolid phosphate is adjusted based on potency of the drug substance lot used.
[2]The actual amount of mannitol is adjusted based on amount of the drug substance used.
[3]Removed during processing.

Example 14

Powder and Formulation for Injection (R)-3-(4-(2-(2-methyltetrazol-5-yl)pyridin-5-yl)-3-fluorophenyl)-5-hydroxymethyl oxazolidin-2-one dihydrogen phosphate 1 (R=$PO(OH)_2$) ") ("Torezolid Phosphate for Injection" or "TR-701 FA for Injection"), 200 mg/vial, was prepared in a formulation as a sterile lyophilized powder for injection. TR-701 FA for Injection is formulated in situ as the disodium salt using sodium hydroxide to take advantage of its superior aqueous solubility (>130 mg/mL).

TR-701 FA for Injection, 200 mg/vial, is to be reconstituted with 4 mL of Sterile Water for Injection (WFI), USP to yield a 50 mg/mL solution. The appropriate clinical dose volume is to be withdrawn from the vial and added to an intravenous (IV) non-di(2-ethylhexyl)phthalate (DEHP) bag containing either 0.9% Sodium Chloride Injection, USP (saline) or 5%

Dextrose Injection, USP (dextrose). The resulting IV solution is to be infused using a non-DEHP solution set with a 0.22 μm in-line filter.

The unit composition of TR-701 FA Compounding Solution for Lyophilization is presented in Table 7 and the unit composition of TR-701 FA for Injection, 200 mg/vial is presented in Table 8.

TABLE 7

Unit Composition of TR-701 FA Compounding Solution for Lyophilization

| Component | Function | Theoretical Quantity |
|---|---|---|
| TR-701 FA | Drug Substance | 100 mg/mL |
| Mannitol, Powder, USP | Bulking Agent | 50 mg/mL |
| Sodium Hydroxide, USP | In-situ salt formation, pH adjustment | qs for pH adjustment to 7.75 |
| Hydrochloric Acid, NF | pH adjustment | qs for pH adjustment to 7.75 |
| Water for Injection, USP/EP | Manufacturing solvent | qs to 1.0 mL |

TABLE 8

Unit Composition of TR-701 FA for Injection, 200 mg/vial

| Component | Function | Theoretical Quantity |
|---|---|---|
| TR-701 FA | Drug Substance | 210 mg$^a$ |
| Mannitol, Powder, USP | Bulking Agent | 105 mg |
| Sodium Hydroxide, USP | In-situ salt formation, pH adjustment | qs for pH adjustment to 7.75 |
| Hydrochloric Acid, NF | pH adjustment | qs for pH adjustment to 7.75 |
| Water for Injection, USP/EP$^b$ | Manufacturing solvent | qs to 2.1 mL |

$^a$A volume equivalent to 210 mg of TR-701 FA is filled into each vial to so that reconstitution of the vial with 4.0 mL of Water for Injection (a final volume of 4.2 mL is obtained due to volume displacement of the dissolved solids) results in a 50 mg/mL solution of TR-701 FA that will allow withdrawal of the label contents.
$^b$Water for Injection is essentially removed during lyophilization.

The typical manufacturing batch formula for TR-701 FA for Injection, 200 mg/vial is presented in Table 9.

TABLE 9

Typical Batch Formula for TR-701 FA for Injection, 200 mg/vial

| Material | Theoretical Quantity |
|---|---|
| TR-701 FA | 400 g$^a$ |
| Mannitol, Powder, USP | 200 g |
| Sodium Hydroxide, NF | qs for pH adjustment to pH 7.75 |
| Hydrochloric Acid, NF | qs for pH adjustment to pH 7.75 |
| Water for Injection, USP/EP | qs 4276 g |
| Total | 4000 mL (~1900 vials) |

$^a$The actual quantity of TR-701 FA drug substance to be weighed is adjusted based on potency.

Figure 8:
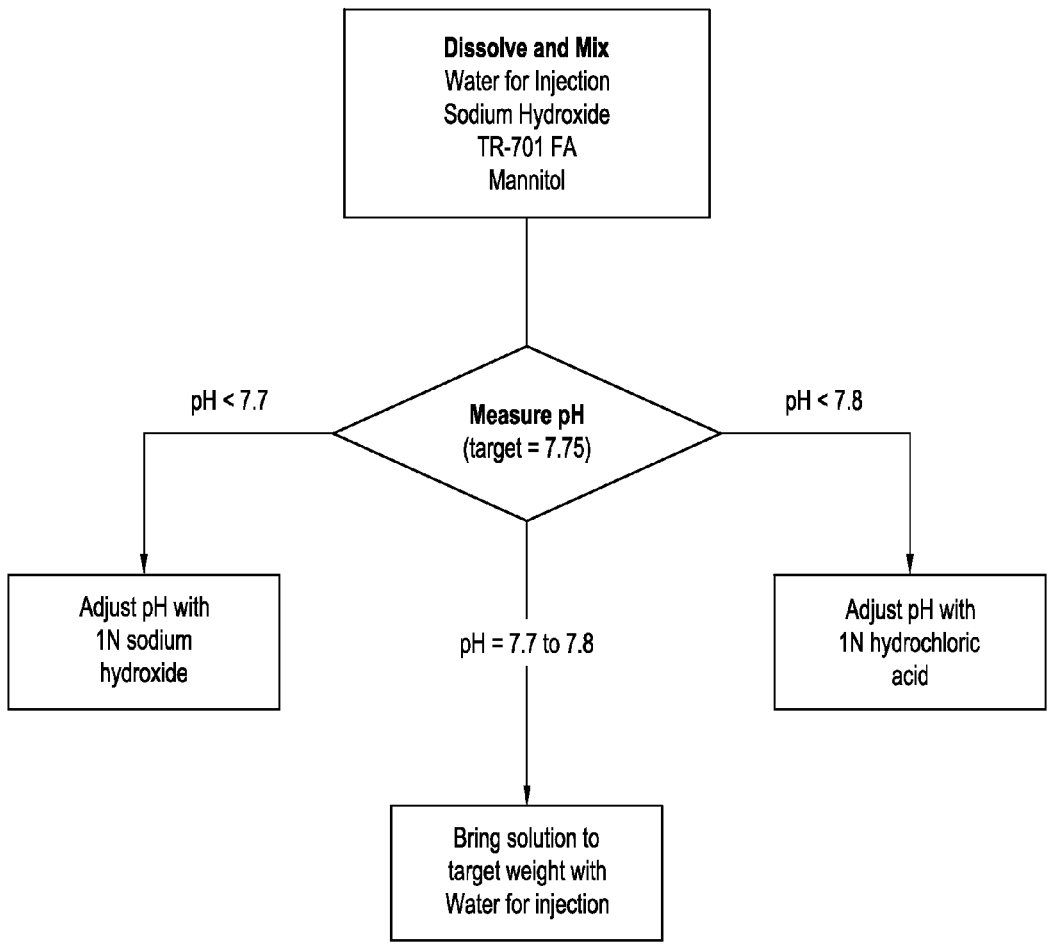
FIG. 8 is a manufacturing process schematic for 1 (R=PO(OH)$_2$) (TR-701 FA) Compounding Solution for Lyophilization.
Figure 9:
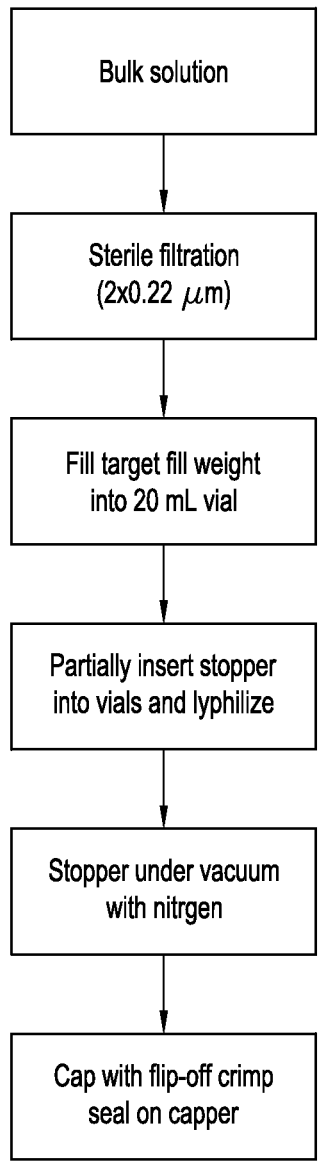
FIG. 9 is a manufacturing process schematic for 1 (R=PO(OH)$_2$) (TR-701 FA) for Injection, 200 mg/vial: sterile filtering, filling, and lyophilization.

The manufacturing process is summarized below and schematics of the process for preparing a compounding solution and for sterile filtering, filling, and lyophilization are presented FIGS. 8 and 9.

Compounding Solution

The compounding solution is prepared in the following sequence:

Add approximately 50% of the total amount of Water for Injection to a tared compounding vessel.

Add TR-701 FA and slowly neutralize with a solution of sodium hydroxide while mixing.

Add and dissolve mannitol with mixing.

Measure the pH of the resulting solution. If the solution is outside the target range of pH 7.70 to 7.80, adjust the pH using either 1N sodium hydroxide or 1N hydrochloric acid.

Add Water for Injection to final volume and mix.

Sterile Filtering/Filling/Lyophilization

Filter the bulk solution through 2 integrity-tested 0.22 μm filters in series and collect the solution in a sterile receiving vessel.

Add target fill weight of solution into 20 mL vials under aseptic conditions.

Partially insert lyophilization stoppers into the vials.

Lyophilize the vials according to an appropriate cycle.

At the end of the lyophilization cycle, backfill the chamber with nitrogen and stopper vials under partial vacuum.

Seal vials with flip off caps.

Example 15

A sample of crystalline free acid which was made according to a method of making the free acid disclosed in U.S. patent application Ser. No. 12/577,089, which is assigned to the same assignee as in the present application, and by using the crystallization methods described herein, was crystallized according to methods described herein was characterized using HPLC and contains various levels of impurities such as those described in Table 10 below:

TABLE 10

| Identified Individual Impurities | HPLC (TM.1911) | NMT | 0.5% | Rx600013 |
|---|---|---|---|---|
| | | NMT | 0.5% | Rx600024 |
| | | NMT | 0.5% | Rx600014 |
| | | NMT | 0.2% | Rx600023 |
| | | NMT | 0.5% | Rx600025 |
| | | NMT | 0.5% | Rx600020 |
| | | NMT | 2.0% | Rx600001 |
| | | NMT | 1.5% | Rx600022 |

In addition, a substantially pure sample of crystalline free acid which was made according to processes that were not disclosed in US Patent Publication No. 20070155798 and was crystallized according to methods described herein (hereinafter "ours"), was compared to a sample of material made by Dong-A Pharm. Co. (hereinafter "the Dong-A material"), which was given to Trius Therapeutics Inc. in approximately 2007. The potency of the Dong-A material was approximately 84% by weight of the sample in comparison to a substantially pure reference sample; however, the purity of the crystalline free acid was 94.1% by weight of the material identified by HPLC as indicated below. Therefore, approximately 10% of the impurities in the Dong-A material was not identified by HPLC. The purity profile comparison is set forth in Table 11 below:

TABLE 11

| Impurity | | Area Percent | | |
|---|---|---|---|---|
| Name | RRT | Dong A | ours | ID |
| 600011 | 0.54 | 0.12 | ND | DA-1dimer diphos |
| 600013** | 0.56 | ND | 0.08 | Des-Me |
| UNK | 0.65 | 0.07 | ND | |
| UNK | 0.77 | 0.34 | ND | |
| UNK | 0.86-0.88 | 0.07 | 0.03 | |
| 600024 | 0.91 | 0.22 | 0.12 | Pyrophosphate |
| UNK | 0.94 | 0.07 | ND | |
| UNK | 0.95 | 0.05 | ND | |
| 600012 | 1 | 94.1 | 97.1 | API |
| 600023 | 1.08 | 0.14 | ND | N-1 Phosphorylated |
| UNK | 1.1 | 0.06 | ND | |
| UNK | 1.14 | 0.05 | ND | |
| 600025** | 1.15 | ND | 0.27 | Over-Alk'd pair |

TABLE 11-continued

| Impurity Name | RRT | Area Percent Dong A | Area Percent ours | ID |
|---|---|---|---|---|
| UNK | 1.2 | 0.07 | ND | |
| UNK | 1.21 | 0.05 | ND | |
| UNK | 1.31 | 0.05 | ND | |
| UNK | 1.39 | 0.26 | 0.04 | |
| UNK | 1.47 | 0.35 | ND | |
| 600020 | 1.5-1.51 | 0.2 | 0.08 | Dimer |
| UNK | 1.56 | ~0.05 | ND | |
| 600001* | 1.67-1.688 | 1.12 | 0.63 | TR-700 |
| 600022 | 1.72-1.73 | 0.28 | 1.2 | Bis |

TABLE 11-continued

| Impurity Name | RRT | Area Percent Dong A | Area Percent ours | ID |
|---|---|---|---|---|
| 600042** | 1.79 | ND | 0.12 | OA-700 mixed di ester |
| 600043** | 1.8 | ND | 0.15 | OA-700 mixed di ester |
| 600026* | 2.27-2.28 | 2.17 | 0.06 | Chloro |
| UNK | 2.34 | 0.05 | ND | |
| UNK | 2.4 | 0.06 | ND | |

*equals ours << Dong A
**equals impurity present in ours but not Dong A

| Organic Impurities in TR-701 FA Drug Substance | |
|---|---|
| Impurity 'Name' | Structure and Chemical Name |
| Rx600013 'Des-methyl TR-701' | 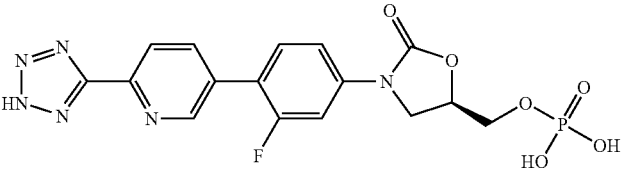 [SMILES: O=C1O[C@@H](COP(=O)(O)O)CN1c1ccc(-c2ccc(-c3nn[nH]n3)nc2)c(F)c1] dihydrogen ((5R)-3-{3-fluoro-4-[6-(2H-1,2,3,4-tetrazol-5-yl)-3-pyridinyl]phenyl}-2-oxo-1,3-oxazolan-5-yl)methyl phosphate |
| Rx600024 'Pyrophosphate' | 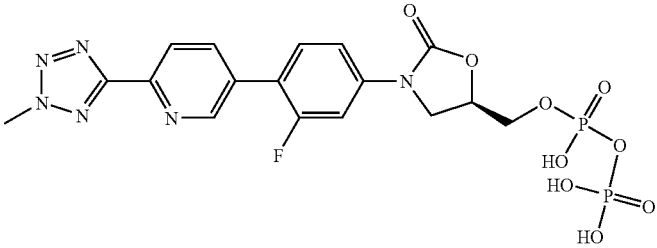 [SMILES: Cn1nnc(-c2ccc(-c3ccc(N4C[C@H](COP(=O)(O)OP(=O)(O)O)OC4=O)cc3F)cn2)n1] trihydrogen ((5R)-3-{3-fluoro-4-[6-(1-methyl-1H-1,2,3,4-tetraazol-5-yl)-3-pyridinyl]phenyl}-2-oxo-1,3-oxazolan-5-yl)methyl pyrophosphate |
| Rx600014 'Ring opened' | 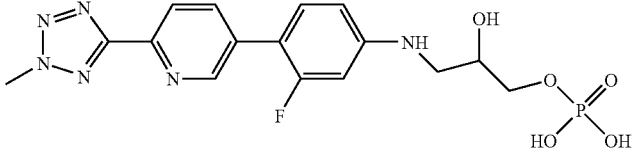 [SMILES: Cn1nnc(-c2ccc(-c3ccc(NCC(O)COP(=O)(O)O)cc3F)cn2)n1] dihydrogen 3-{3-fluoro-4-[6-(2-methyl-2H-1,2,3,4-tetraazol-5-yl)-3-pyridinyl]aniline}-2-hydroxypropyl phosphate |
| Rx600023 'Me-isomer' | 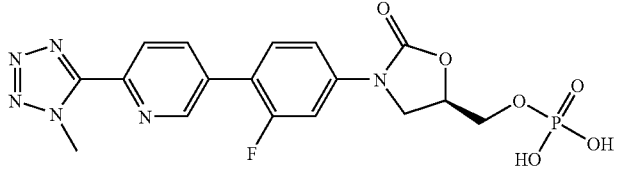 [SMILES: Cn1nnnc1-c1ccc(-c2ccc(N3C[C@H](COP(=O)(O)O)OC3=O)cc2F)cn1] dihydrogen ((5R)-3-{3-fluoro-4-[6-(1-methyl-1H-1,2,3,4-tetraazol-5-yl)-3-pyridinyl]phenyl}-2-oxo-1,3-oxazolan-5-yl)methyl phosphate |

-continued

Organic Impurities in TR-701 FA Drug Substance

| Impurity 'Name' | Structure and Chemical Name |
|---|---|
| Rx600025 'Overalkylated-phosphorylated impurity' | 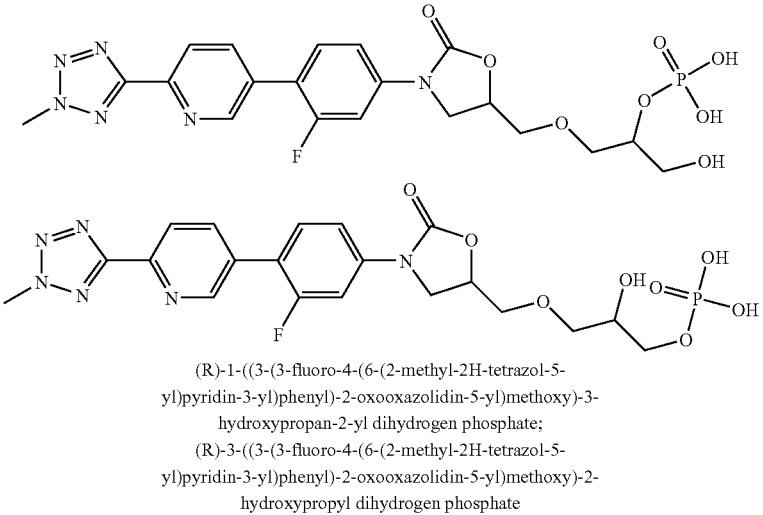<br>(R)-1-((3-(3-fluoro-4-(6-(2-methyl-2H-tetrazol-5-yl)pyridin-3-yl)phenyl)-2-oxooxazolidin-5-yl)methoxy)-3-hydroxypropan-2-yl dihydrogen phosphate;<br>(R)-3-((3-(3-fluoro-4-(6-(2-methyl-2H-tetrazol-5-yl)pyridin-3-yl)phenyl)-2-oxooxazolidin-5-yl)methoxy)-2-hydroxypropyl dihydrogen phosphate |
| Rx600020 'Dimer impurity' | 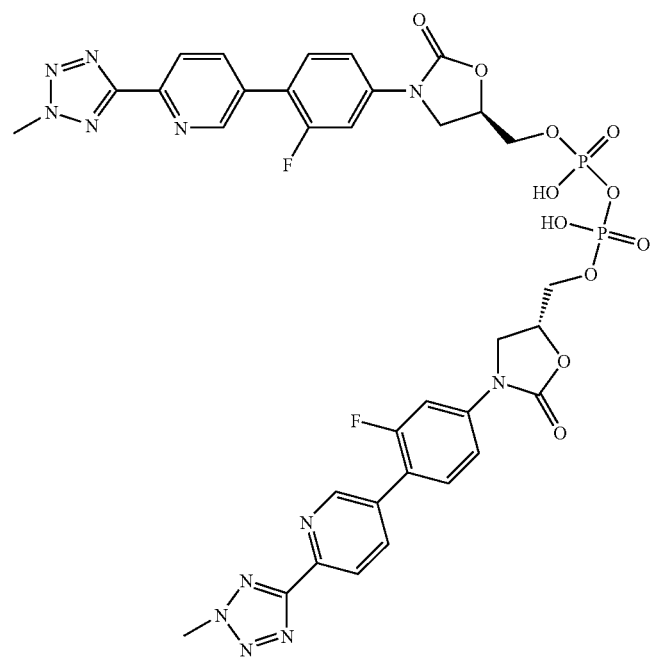<br>dihydrogen bis-O-O'-[(5R)-3-{3-fluoro-4-[6-(2-methyl-2H-1,2,3,4-tetrazol-5-yl)-3-pyridinyl]phenyl}-2-oxo-1,3-oxazolidin-5-yl]methyl pyrophosphate |
| Rx600026 "Chloro" | 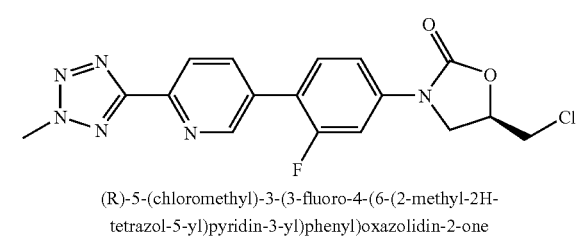<br>(R)-5-(chloromethyl)-3-(3-fluoro-4-(6-(2-methyl-2H-tetrazol-5-yl)pyridin-3-yl)phenyl)oxazolidin-2-one |

| Organic Impurities in TR-701 FA Drug Substance | |
|---|---|
| Impurity 'Name' | Structure and Chemical Name |
| Rx600001 TR-700 | 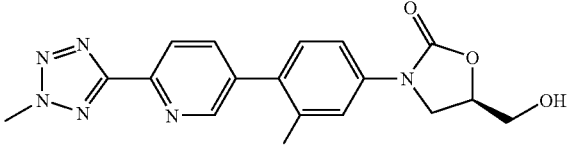  5R)-3-{3-Fluoro-4-[6-(2-methyl-2H-1,2,3,4-tetrazol-5-yl)-pyridin-3-yl]-phenyl}-5-hydroxymethyl-1,3-oxazolidin-2-one |
| Rx600022 'Bis phosphate' | 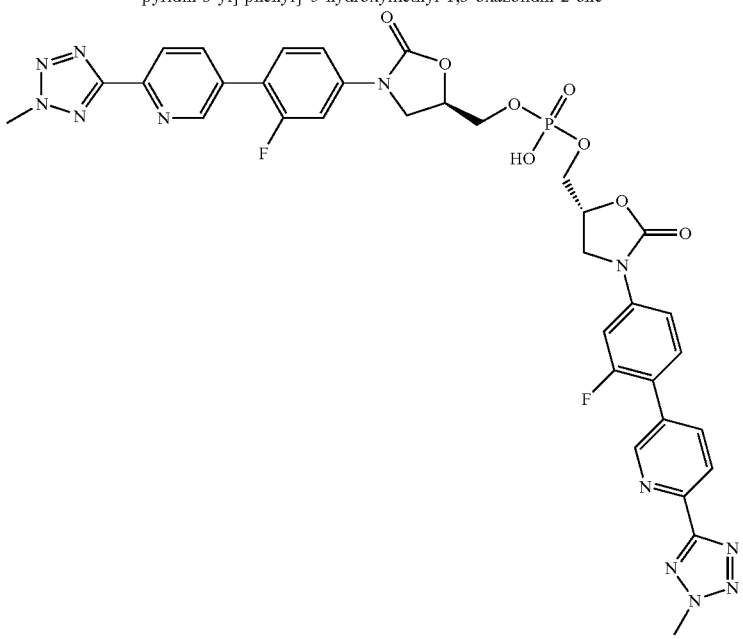  hydrogen bis-O-O'-[(5R)-3-{3-fluoro-4-[6-(2-methyl-2H-1,2,3,4-tetrazol-5-yl)-3-pyridinyl]phenyl}-2-oxo-1,3-oxazolidin-5-yl]methyl phosphate |
| Rx600042 | 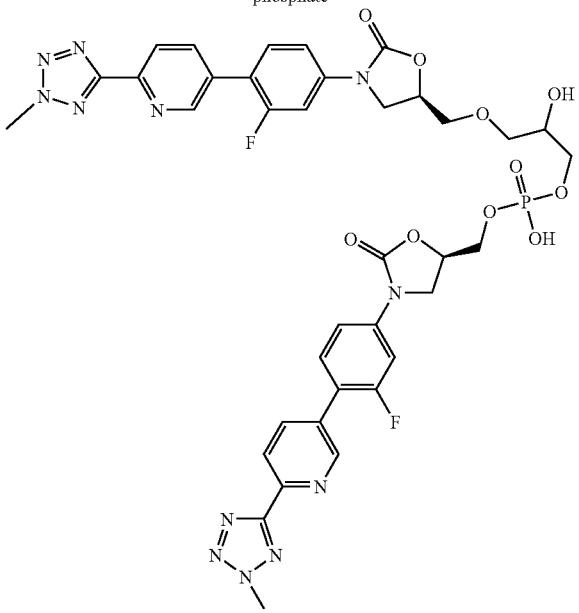  3-{[(5R)-3-{3-fluoro-4-[6-(2-methyl-2H-tetrazol-5-yl)pyridin-3-yl]phenyl}-2-oxo-1,3-oxazolidin-5-yl]methoxy}-2-hydroxypropyl [(5R)-3-{3-fluoro-4-[6-(2-methyl-2H-tetrazol-5-yl)pyridin-3-yl]phenyl}-2-oxo-1,3-oxazolidin-5-yl]methyl hydrogen phosphate |

-continued

| Organic Impurities in TR-701 FA Drug Substance | |
|---|---|
| Impurity 'Name' | Structure and Chemical Name |
| Rx600043 | 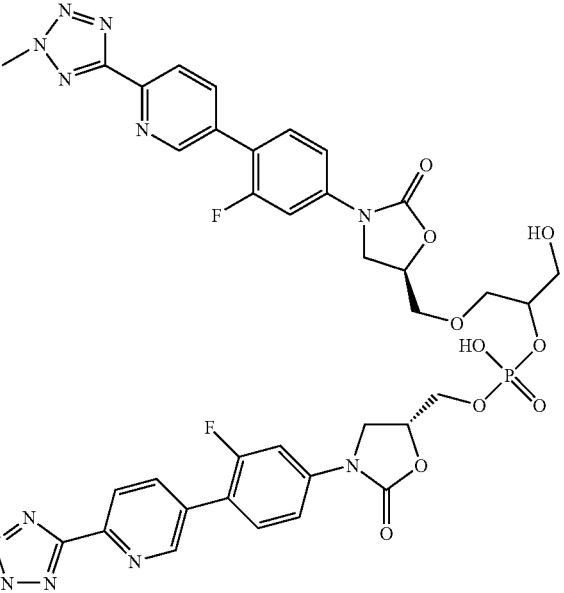<br>2-{[(5R)-3-{3-fluoro-4-[6-(2-methyl-2H-tetrazol-5-yl)pyridin-3-yl]phenyl}-2-oxo-1,3-oxazolidin-5-yl]methoxy}-1-hydroxyethyl [(5R)-3-{3-fluoro-4-[6-(2-methyl-2H-tetrazol-5-yl)pyridin-3-yl]phenyl}-2-oxo-1,3-oxazolidin-5-yl]methyl hydrogen phosphate |

What is claimed is:

1. Crystalline particles comprising
   at least about 96% by weight of (R)-3-(4-(2-(2-methyltetrazol-5-yl)pyridin-5-yl)-3-fluoro-phenyl)-5-hydroxymethyl oxazolidin-2-one dihydrogen phosphate,
   wherein the remainder of the crystalline particles comprises at least one compound selected from the group consisting of

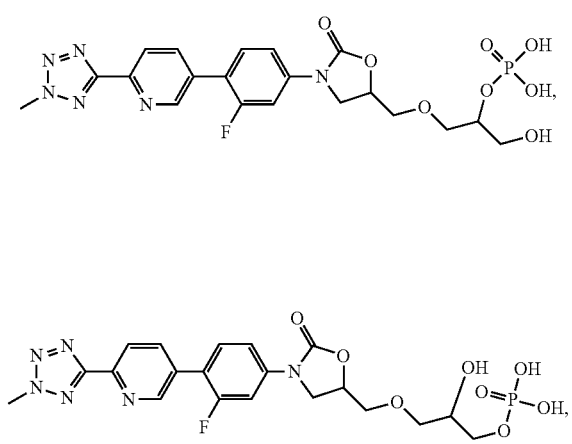

-continued

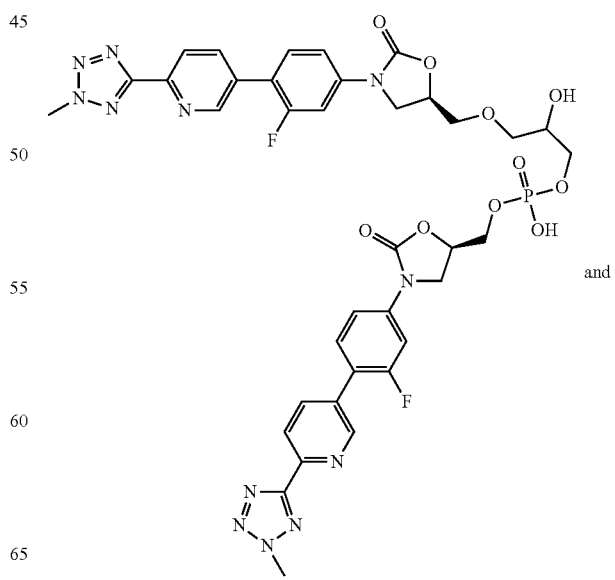

and

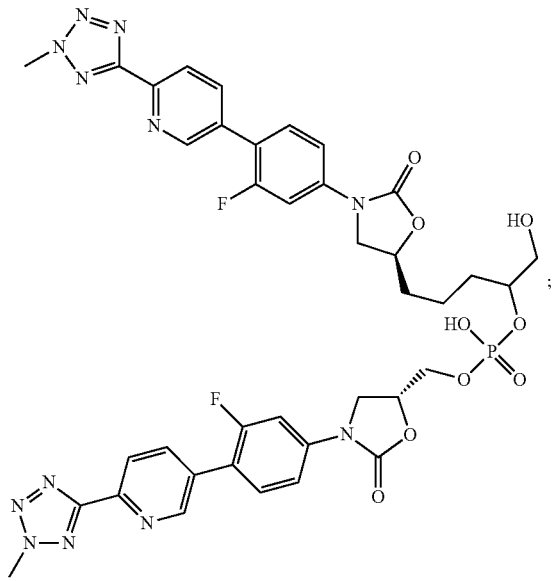

wherein the median volume diameter of the crystalline particles is at least about 1.0 µm; 90% of the total particle volume of the particles has an average diameter of at least about 45 µm; and/or 10% of the total particle volume of the particles has an average diameter of at least about 0.5 µm; and wherein the crystalline particles have an X-ray powder diffraction pattern comprising the following peaks: 14.7°, 15.2°, 16.6°, 20.3°, 26.8°, and 28.2°.

2. The purified crystalline particles of claim 1 further comprising less than 1% by weight of (R)-5-(chloromethyl)-3-(3-fluoro-4-(6-(2-methyl-2H-tetrazol-5-yl)pyridin-3-yl)phenyl)oxazolidin-2-one having the following structure:

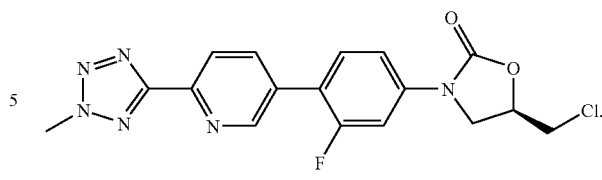

3. The crystalline particles of claim 2 comprising at least about 97% by weight of (R)-3-(4-(2-(2-methyltetrazol-5-yl) pyridin-5-yl)-3-fluorophenyl)-5-hydroxymethyl oxazolidin-2-one dihydrogen phosphate.

4. The crystalline particles of claim 1 further comprising less than 1% by weight of a compound having the following structure:

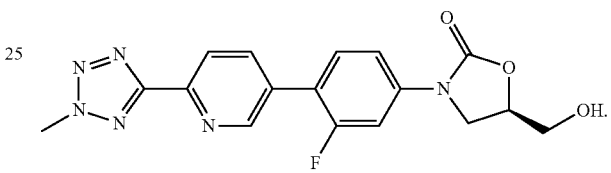

5. The crystalline particles of claim 4 comprising at least about 97% by weight of (R)-3-(4-(2-(2-methyltetrazol-5-yl) pyridin-5-yl)-3-fluorophenyl)-5-hydroxymethyl oxazolidin-2-one dihydrogen phosphate.

6. Crystalline particles comprising
at least about 96% by weight of (R)-3-(4-(2-(2-methyltetrazol-5-yl)pyridin-5-yl)-3-fluoro-phenyl)-5-hydroxymethyl oxazolidin-2-one dihydrogen phosphate; and at least one compound selected from the group consisting of

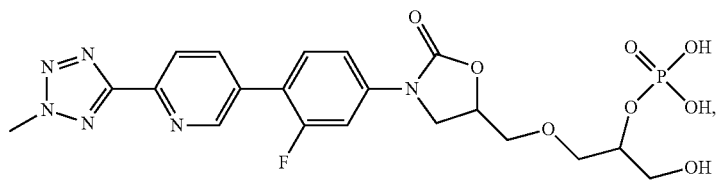

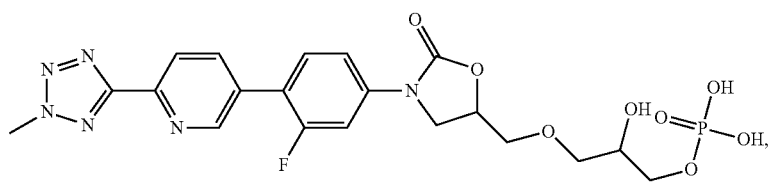 [SMILES: Cn1nnc(-c2ccc(-c3ccc(N4CC(COCC(O)COP(=O)(O)O)OC4=O)cc3F)cn2)n1]

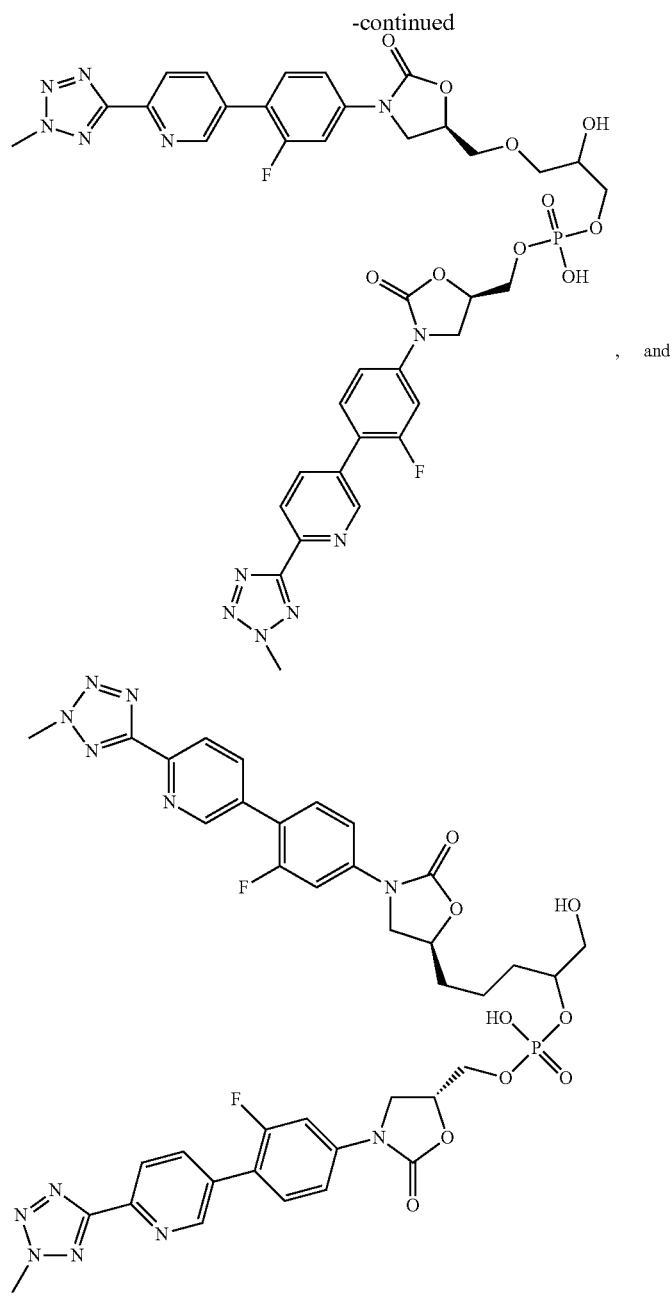

wherein the crystalline particles have an X-ray powder diffraction pattern comprising the following peaks: 14.7°, 15.2°, 16.6°, 20.3°, 26.8°, and 28.2°.

7. The crystalline particles of claim 1, wherein the median volume diameter is at least about 1.0 μm.

8. The crystalline particles of claim 1, characterized by a DSC pattern having endo-endo peaks at about 255-258° C.

9. A pharmaceutical composition comprising the crystalline particles of claim 1 and at least one pharmaceutically acceptable carrier, excipient or diluent;
wherein the crystalline particles are crystalline particles in the pharmaceutical composition.

10. The pharmaceutical composition of claim 9 wherein the pharmaceutically acceptable carrier, excipient or diluent is at least one member selected from the group consisting of mannitol, polyvinylpyrrolidone, cross-linked polyvinylpyrrolidone, and magnesium stearate.

11. A reaction mixture comprising the crystalline particles of claim 6 and a base.

12. The reaction mixture of claim 11, wherein the base is sodium hydroxide.

13. A pharmaceutical composition comprising a lyophilisate of the reaction mixture of claim 11, comprising

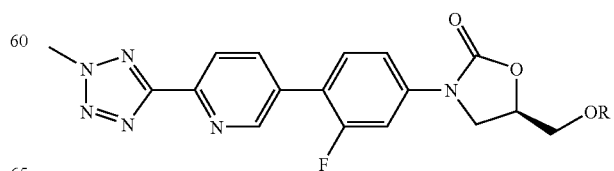

wherein R=PO(ONa)$_2$.

14. A pharmaceutical composition comprising a combination of at least about 96% by weight of a compound having the following structure:

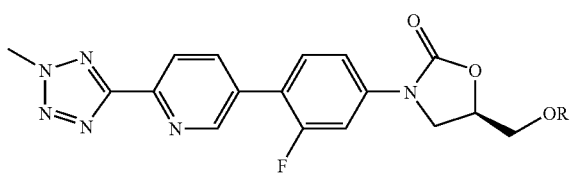

wherein R=PO(ONa)₂; and wherein the remainder of the combination comprises at least one salt of a compound selected from the group consisting of:

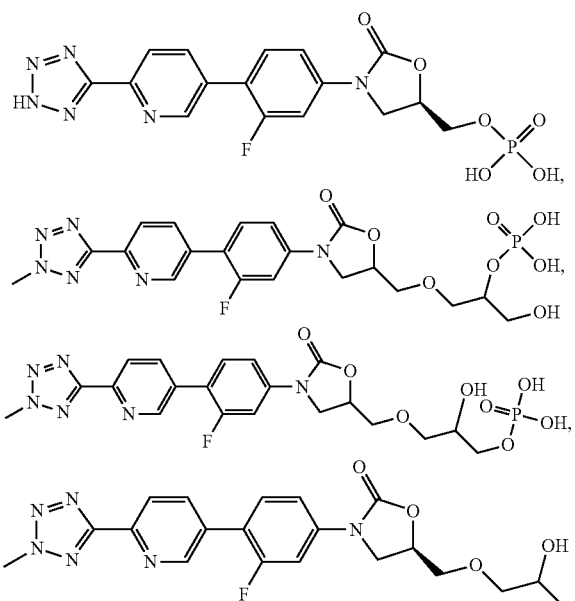

and

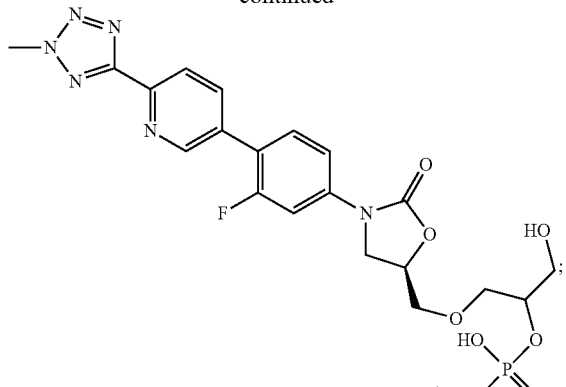

and at least one pharmaceutically acceptable carrier, excipient or diluent.

15. The pharmaceutical composition of claim 14 wherein the combination further comprises less than 1% by weight of

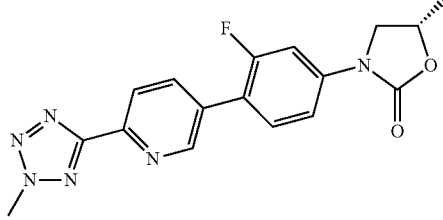

16. The pharmaceutical composition of claim 15 wherein the combination comprises at least about 97% by weight of

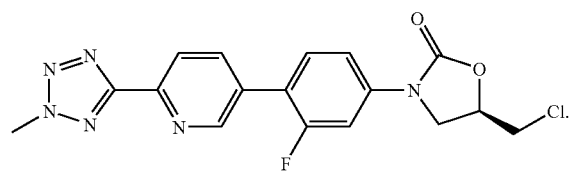

wherein R=PO(ONa)₂.

17. The pharmaceutical composition of claim 14 wherein the combination further comprises less than 1% by weight of

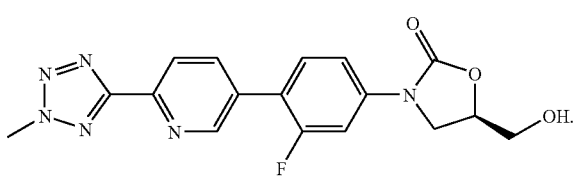 [SMILES: Cn1nnc(-c2ccc(-c3ccc(N4C[C@H](CO)OC4=O)cc3F)cn2)n1]

18. The pharmaceutical composition of claim 17 wherein the combination comprises at least about 97% by weight of

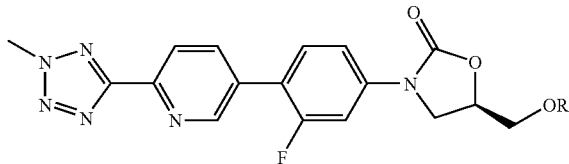

wherein R=PO(ONa)$_2$.

19. A method of treating a bacterial infection comprising administering an effective amount of the crystalline particles of claim 1 to a subject in need thereof.

20. A method of treating a bacterial infection comprising administering an effective amount of the pharmaceutical composition of claim 14 to a subject in need thereof.

21. A process for making the crystalline particles of claim 6, comprising
drying the crystalline particles.

22. The process of claim 21 further comprising filtering the crystalline particles from a supernatant before the drying step.

23. The process of claim 22 further comprising
immediately contacting a salt of crystalline (R)-3-(4-(2-(2-methyltetrazol-5-yl)-pyridin-5yl)-3-fluorophenyl)-5-hydroxymethyl oxazolidin-2-one dihydrogen phosphate with an acid solution to form crystallized (R)-3-(4-(2-(2-methyltetrazol-5-yl)pyridin-5-yl)-3-fluorophenyl)-5-hydroxymethyl oxazolidin-2-one dihydrogen phosphate before the filtering step.

24. The process of claim 23
wherein the acid solution comprises HCl and ethanol, or HCl and THF.

25. A process for making the crystalline particles of claim 1, comprising
drying the crystalline particles.

26. A pharmaceutical composition comprising the crystalline particles of claim 6 and at least one pharmaceutically acceptable carrier, excipient or diluent;
wherein the crystalline particles are crystalline particles in the pharmaceutical composition.

27. A method of treating a bacterial infection comprising administering an effective amount of the crystalline particles of claim 6 to a subject in need thereof.

* * * * *

UNITED STATES PATENT AND TRADEMARK OFFICE
CERTIFICATE OF CORRECTION

PATENT NO.       : 8,426,389 B2  
APPLICATION NO.  : 12/699864  
DATED            : April 23, 2013  
INVENTOR(S)      : Reichenbächer et al.

It is certified that error appears in the above-identified patent and that said Letters Patent is hereby corrected as shown below:

Title Page 1 (item 57, Abstract) at line 9, Change "Staphylococi" to --Staphylococci--.

Title Page 1 (item 57, Abstract) at line 10, Change "Streptococi," to --Streptococci,--.

In the Drawings:

Sheet 7 of 14 (FIG. 5) at line 18 (approx.), Change "Atmosphare" to --Atmosphere--.

Sheet 8 of 14 (FIG. 6) at line 16 (approx.), Change "Projeckt" to --Project--.

Figure 7:
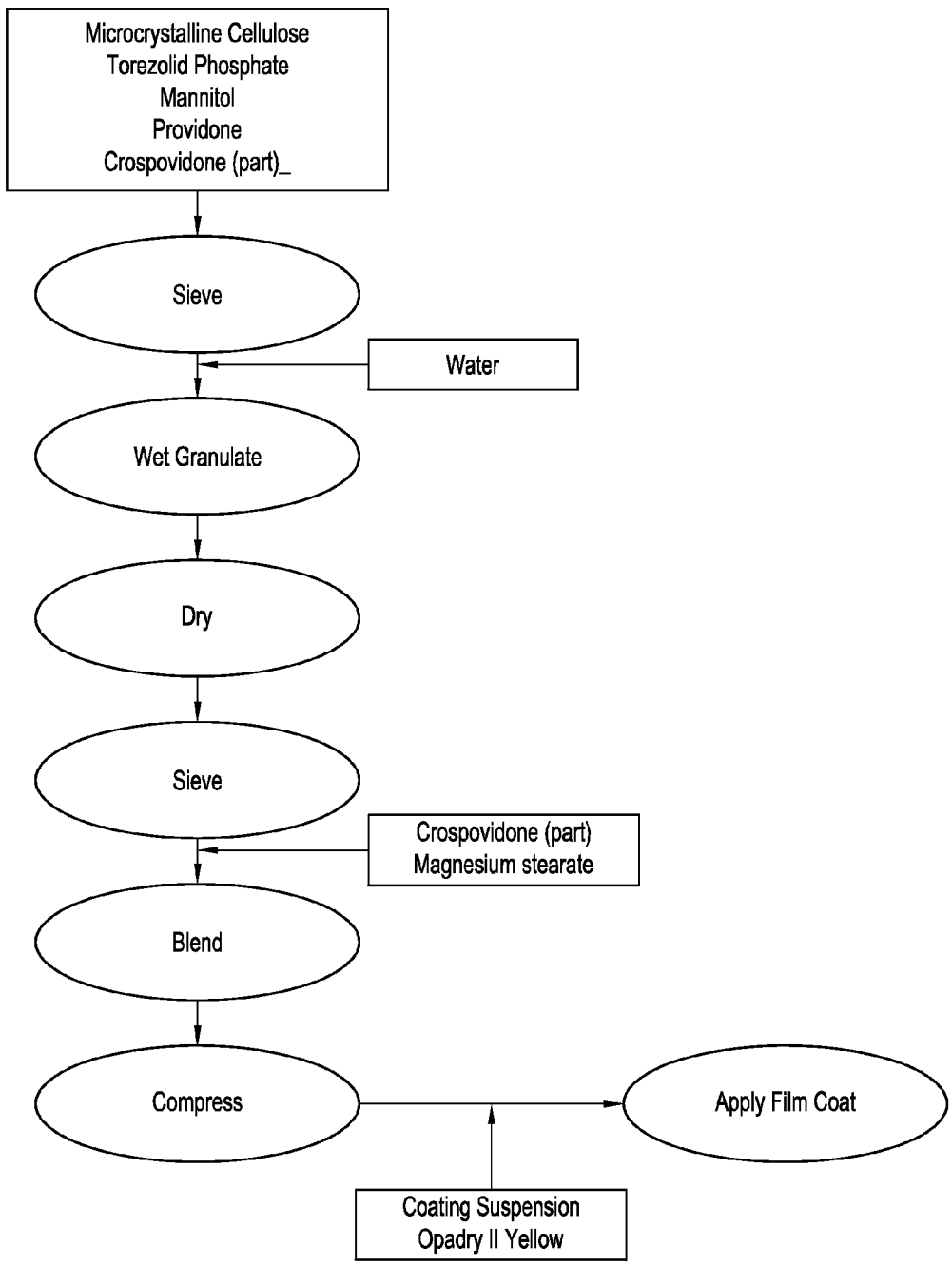
FIG. 7 is a manufacturing process schematic for 1 (R=PO(OH)$_2$) (TR-701 FA) in a tablet dosage form.

Sheet 9 of 14 (FIG. 7) at line 1, Change "manafacturing" to --manufacturing--.

Sheet 11 of 14 (FIG. 9) at line 11, Change "nitrgen" to --nitrogen--.

In the Specification:

In column 3 at line 25, Change "hydroxy-methyl" to --hydroxymethyl--.

In column 5 at line 18, Change "methyl]tetrazol" to --methyltetrazol--.

In column 6 at line 41 (approx.), Change "solvents" to --solvents.--.

In column 15 at line 64, Change "Staphylococi" to --Staphylococci--.

In column 15 at line 65, Change "Streptococi" to --Streptococci--.

In column 19 at line 66, Change "stifling" to --stirring--.

In column 20 at line 37, Change "Salts" to --Salts:--.

In column 20 at lines 54-55 (approx.), Change "C, 43.9 (44.8); H, 3.6 (3.7); N, 18.1 (18.4); O, 21.2 (22.1); F, 4.2 (4.2); P, 6.7 (6.8)." to --C 43.9 (44.8); H 3.6 (3.7); N 18.1 (18.4); O 21.2 (22.1); F 4.2 (4.2); P 6.7 (6.8).--.

Signed and Sealed this  
First Day of April, 2014

Michelle K. Lee  
*Deputy Director of the United States Patent and Trademark Office*

CERTIFICATE OF CORRECTION (continued)
U.S. Pat. No. 8,426,389 B2

In the Claims:

In columns 33 (Structure 1) at lines 1-29 (approx.), In Claim 1,

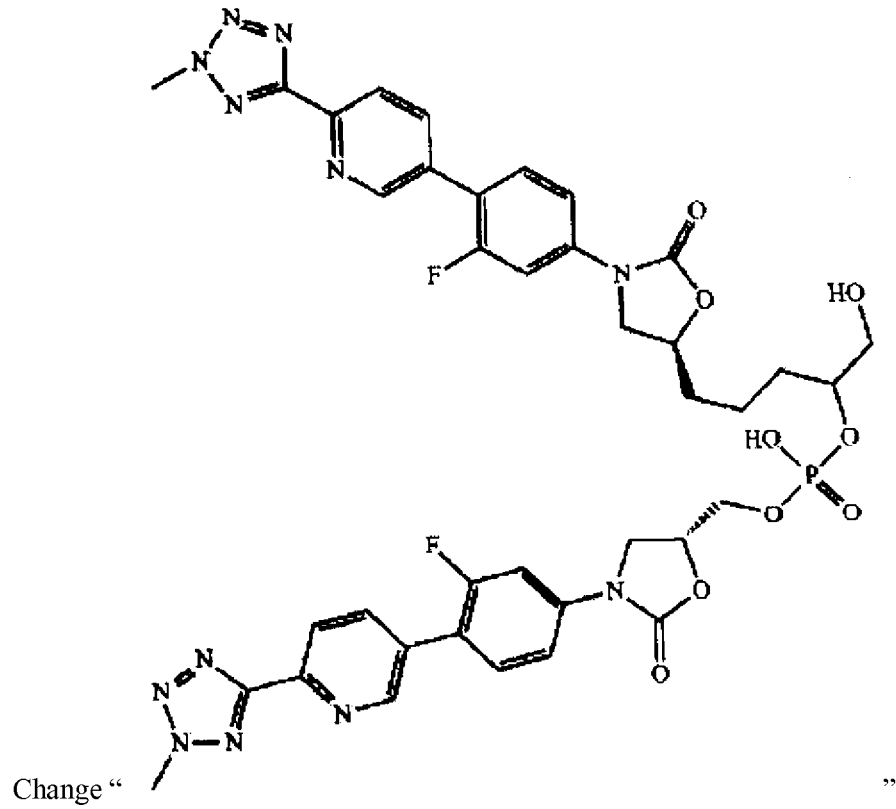

Change " " " "

CERTIFICATE OF CORRECTION (continued)
U.S. Pat. No. 8,426,389 B2 to -- 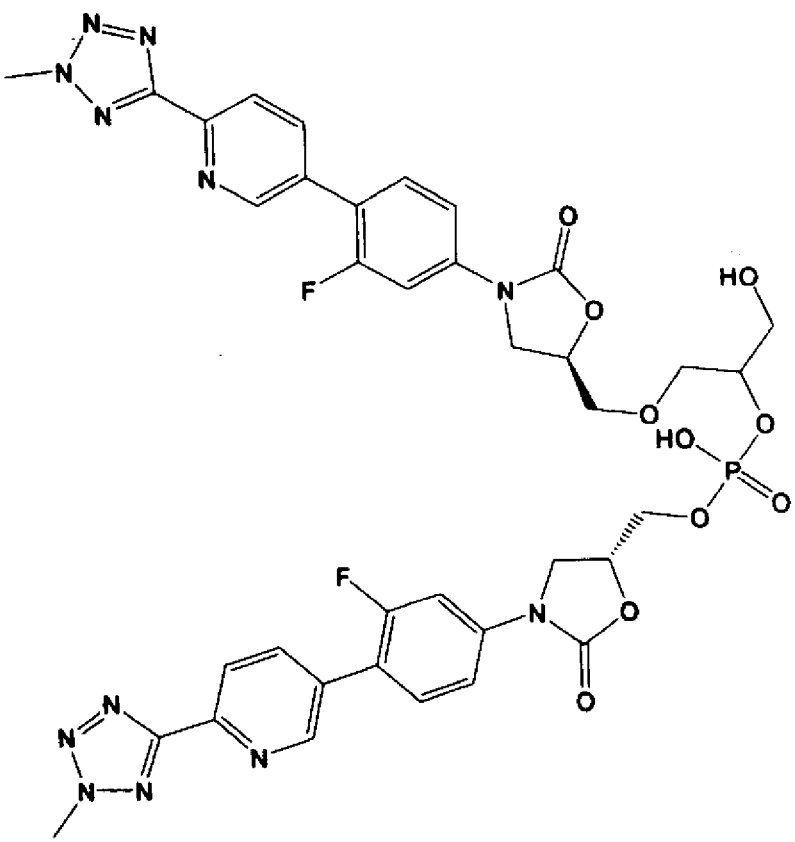 --.

In column 33 at line 40, In Claim 2, After "The" delete "purified".

In columns 35-36 (Structure 2), In Claim 6,

Change " 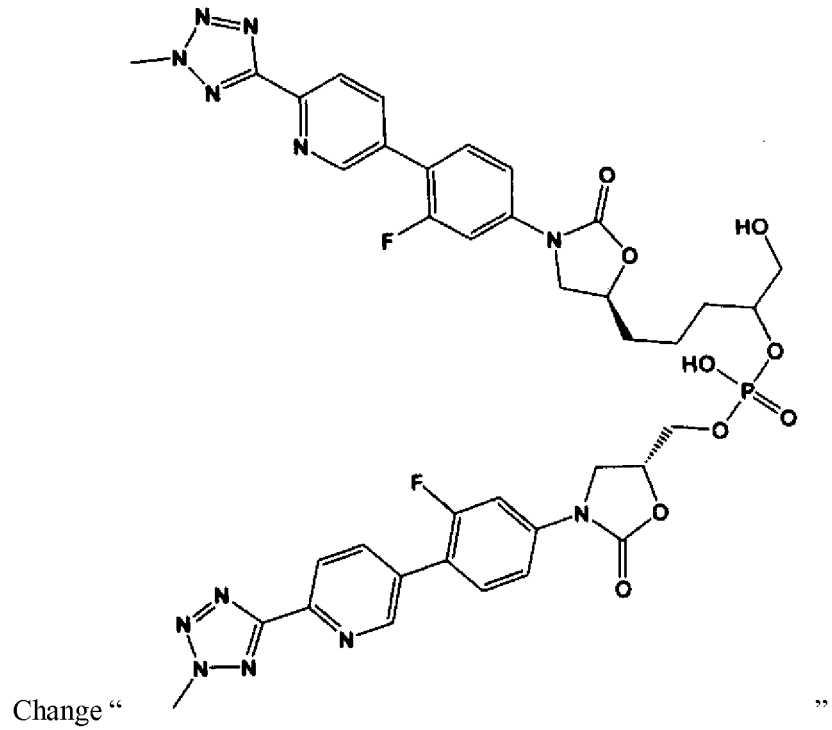 "

CERTIFICATE OF CORRECTION (continued)
U.S. Pat. No. 8,426,389 B2 to --
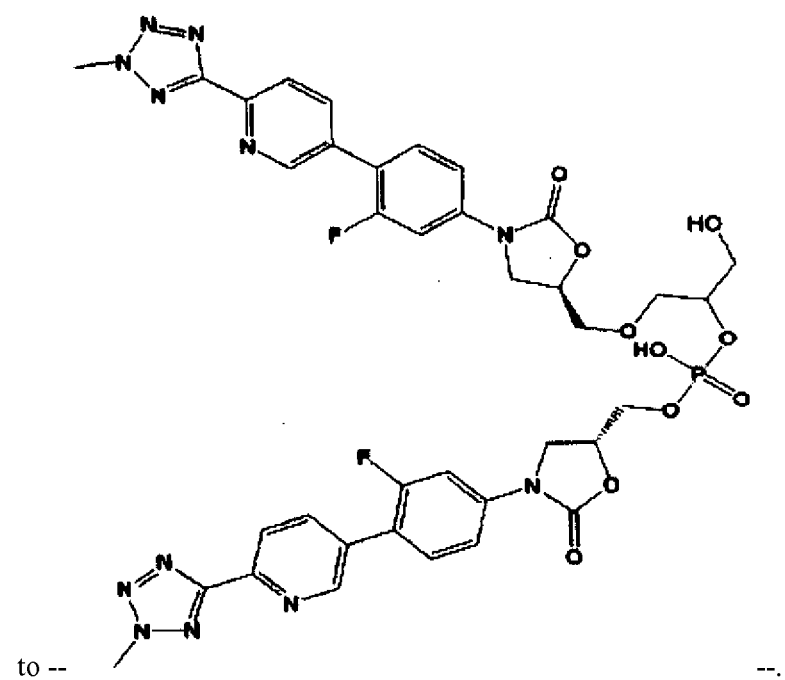
--.

In column 40 at line 3, In Claim 23, Change "5yl" to --5-yl--.